(12) United States Patent
Otsu et al.

(10) Patent No.: US 10,109,800 B2
(45) Date of Patent: *Oct. 23, 2018

(54) ORGANIC ELECTROLUMINESCENT ELEMENT, DISPLAY DEVICE AND LIGHTING DEVICE

(71) Applicant: Konica Minolta, Inc., Chiyoda-ku, Tokyo (JP)

(72) Inventors: Shinya Otsu, Hiro (JP); Eisaku Katoh, Hachioji (JP); Tatsuo Tanaka, Sagamihara (JP)

(73) Assignee: KONICA MINOLTA, INC., Tokyo (JP)

( * ) Notice: Subject to any disclaimer, the term of this patent is extended or adjusted under 35 U.S.C. 154(b) by 24 days.

This patent is subject to a terminal disclaimer.

(21) Appl. No.: 15/340,520

(22) Filed: Nov. 1, 2016

(65) Prior Publication Data

US 2017/0054092 A1 Feb. 23, 2017

Related U.S. Application Data

(63) Continuation of application No. 14/595,611, filed on Jan. 13, 2015, which is a continuation of application (Continued)

(30) Foreign Application Priority Data

Dec. 13, 2006 (JP) .................................. 2006-335664

(51) Int. Cl.
*H01L 51/50* (2006.01)
*H01L 51/00* (2006.01)
(Continued)

(52) U.S. Cl.
CPC ........ *H01L 51/0072* (2013.01); *C07D 405/14* (2013.01); *C07D 409/14* (2013.01); (Continued)

(58) Field of Classification Search
None
See application file for complete search history.

(56) References Cited

U.S. PATENT DOCUMENTS

2002/0045061 A1 4/2002 Hosokawa
2003/0215667 A1 11/2003 Xie
(Continued)

FOREIGN PATENT DOCUMENTS

CN 1365381 A 8/2002
EP 1205527 A1 5/2002
(Continued)

OTHER PUBLICATIONS

Chen C. H. et al.: Stilbene like carbazole dimer-based electroluminescent materials, Tetrahedron, Elseview Science Publishers, Amsterdam, NL, vol. 62, No. 36, Sep. 4, 2006, pp. 8564-8570.
(Continued)

*Primary Examiner* — Gregory D Clark
(74) *Attorney, Agent, or Firm* — Cantor Colburn LLP

(57) ABSTRACT

Disclosed is an organic electroluminescent device having long life, while exhibiting high luminous efficiency. Also disclosed are an illuminating device and a display, each using such an organic electroluminescent device. In the organic electroluminescent device, a compound represented by the general formula (A) which is suitable as a host material for a phosphorescent metal complex is used at least in one sublayer of a light-emitting layer.

12 Claims, 2 Drawing Sheets

Related U.S. Application Data

No. 13/234,601, filed on Sep. 16, 2011, now Pat. No. 9,048,434, which is a continuation of application No. 12/443,410, filed as application No. PCT/JP2007/073777 on Dec. 10, 2007, now Pat. No. 8,541,112.

(51) Int. Cl.

| | | |
|---|---|---|
| *C07D 405/14* | (2006.01) | |
| *C07D 409/14* | (2006.01) | |
| *C07D 413/14* | (2006.01) | |
| *C07D 471/04* | (2006.01) | |
| *C09K 11/06* | (2006.01) | |
| *H05B 33/14* | (2006.01) | |
| *H05B 33/20* | (2006.01) | |
| *C09K 11/02* | (2006.01) | |

(52) U.S. Cl.
CPC ......... *C07D 413/14* (2013.01); *C07D 471/04* (2013.01); *C09K 11/025* (2013.01); *C09K 11/06* (2013.01); *H01L 51/006* (2013.01); *H01L 51/0067* (2013.01); *H01L 51/0071* (2013.01); *H01L 51/0073* (2013.01); *H01L 51/0074* (2013.01); *H01L 51/0081* (2013.01); *H01L 51/0085* (2013.01); *H05B 33/14* (2013.01); *H05B 33/20* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1074* (2013.01); *C09K 2211/1088* (2013.01); *C09K 2211/1092* (2013.01); *C09K 2211/185* (2013.01); *H01L 51/5016* (2013.01)

(56) References Cited

U.S. PATENT DOCUMENTS

| | | |
|---|---|---|
| 2004/0053071 A1 | 3/2004 | Igarashi et al. |
| 2004/0076853 A1 | 4/2004 | Jarikov |
| 2005/0008895 A1 | 1/2005 | Takada et al. |
| 2005/0067951 A1 | 3/2005 | Richter et al. |
| 2005/0222429 A1 | 10/2005 | Hosokawa |
| 2005/0249970 A1 | 11/2005 | Suzuri et al. |
| 2006/0008670 A1 | 1/2006 | Lin et al. |
| 2006/0046098 A1 | 3/2006 | Hosokawa |
| 2006/0051611 A1 | 3/2006 | Brunner et al. |
| 2006/0073347 A1 | 4/2006 | Brunner et al. |
| 2006/0078757 A1 | 4/2006 | Boerner |
| 2006/0251918 A1 | 11/2006 | Iwakuma et al. |
| 2006/0251923 A1 | 11/2006 | Lin et al. |
| 2007/0141387 A1* | 6/2007 | Nakano ............... C09K 11/06 428/690 |
| 2007/0224446 A1 | 9/2007 | Nakano et al. |
| 2009/0017330 A1 | 1/2009 | Iwakuma et al. |
| 2009/0096360 A1 | 4/2009 | Tanaka et al. |
| 2009/0131673 A1 | 5/2009 | Tanabe et al. |

FOREIGN PATENT DOCUMENTS

| | | | |
|---|---|---|---|
| EP | 1486552 A1 | 12/2004 | |
| EP | 1894923 A1 | 3/2008 | |
| EP | 1947911 A1 | 7/2008 | |
| JP | 2002226495 A | 8/2002 | |
| JP | 2002234894 A | 8/2002 | |
| JP | 2002284862 A | 10/2002 | |
| JP | 2002308837 A | 10/2002 | |
| JP | 2002332291 A | 11/2002 | |
| JP | 2002332292 A | 11/2002 | |
| JP | 2002338588 A | 11/2002 | |
| JP | 2003133075 A | 5/2003 | |
| JP | 2004071500 A | 3/2004 | |
| JP | 2004214050 A | 7/2004 | |
| JP | 2004217557 A | 8/2004 | |
| JP | 2004253298 A | 9/2004 | |
| JP | 2004311404 A | 11/2004 | |
| JP | 2004342391 A | 12/2004 | |
| JP | 20052053 A | 1/2005 | |
| JP | 200544791 A | 2/2005 | |
| JP | 2006352045 A | 12/2006 | |
| JP | 2007126403 A | 5/2007 | |
| WO | 0172927 A1 | 10/2001 | |
| WO | 0215645 A1 | 2/2002 | |
| WO | 2004055129 A1 | 7/2004 | |
| WO | 2004055921 A2 | 7/2004 | |
| WO | 2004072205 A2 | 8/2004 | |
| WO | 2005007767 A2 | 1/2005 | |
| WO | 2006009024 A1 | 1/2006 | |
| WO | 2006013738 A1 | 2/2006 | |
| WO | 2006128800 A1 | 12/2006 | |
| WO | 2006137210 A1 | 12/2006 | |
| WO | WO 2006/128800 A1 * | 12/2006 | ............ C09K 11/06 |
| WO | 2007108362 A1 | 9/2007 | |
| WO | 2007111176 A1 | 10/2007 | |

OTHER PUBLICATIONS

Communication Pursuant to Rule 114(2) EPC and Observations by a Third Party Concerning the Patentability of the Invention, European Patent Office, for Application No./Patent No. 07859762.2-1218/2101365 PCT/JP2007073777, dated Oct. 7, 2011.
European Search Report for EP Patent Application 07859762.2, PCT/JP2007/073777 dated May 6, 2011.
Extended European Search Report for Application No. 11196141. 3.-1355/2437326, dated Oct. 16, 2013.
International Search Report for International Application No. PCT/JP2007/073777 dated Mar. 11, 2008 with English Translation.
Japanese Notification of Reasons for Refusal corresponding to Application No. 2014-224106; dated Aug. 18, 2015, with English translation.
Notice of Reasons for Refusal for Japanese Patent Application No. 2008-549306, dated Apr. 9, 2013, with English translation.
Office Action for Japanese Patent Application 2008-549306, dated Aug. 1, 2012, with English translation.
U.S. Final Office Action corresponding to U.S. Appl. No. 13/234,601; dated Jun. 6, 2012.
U.S. Final Office Action corresponding to U.S. Appl. No. 13/234,601; dated Nov. 6, 2014.
U.S. Non Final Office Action corresponding to U.S. Appl. No. 13/234,601; dated Jan. 13, 2012.
U.S. Non Final Office Action corresponding to U.S. Appl. No. 13/234,601; dated May 8, 2014.
U.S. Non Final Office Action corresponding to U.S. Appl. No. 13/967,997 dated Mar. 29, 2016.
U.S. Non Final Office Action corresponding to Application No. 14/595,611; dated Aug. 1, 2016.

* cited by examiner

ORGANIC ELECTROLUMINESCENT ELEMENT, DISPLAY DEVICE AND LIGHTING DEVICE

CROSS REFERENCE TO RELATED APPLICATIONS

The present application is a continuation application of U.S. patent application Ser. No. 14/595,611, filed Jan. 13, 2015, the entire contents of which are incorporated herein by reference and priority to which is hereby claimed. application Ser. No. 14/595,611 is a continuation application of U.S. patent application Ser. No. 13/234,601, filed Sep. 16, 2011. application Ser. No. 13/234,601 is a continuation application of U.S. patent application Ser. No. 12/443,410, filed Mar. 27, 2009. application Ser. No. 12/443,410 is a U.S. National Stage Application of International Application PCT/JP2007/073777, filed Dec. 10, 2007, priority to which is claimed herein and the contents of which are incorporated herein by reference. The PCT/JP2007/073777 application claimed the benefit of the date of the earlier filed Japanese Patent Application No. 2006-335664, filed Dec. 13, 2006, the entire contents of which are incorporated herein by reference, and priority which is hereby claimed.

TECHNICAL FIELD

The present invention relates to an organic electroluminescent element, a display device and a lighting device.

BACKGROUND

Conventionally, an emission type electronic display device includes an electroluminescence display (hereinafter, referred to as an ELD). A constituent element of an ELD includes such as an inorganic electroluminescent element and an organic electroluminescent element (hereinafter, referred to as an organic EL element). An inorganic electroluminescent element has been utilized as a flat light source, however, it requires a high voltage of alternating current to operate an emission element. An organic electroluminescent element is an element provided with a constitution comprising an emitting layer containing a emitting substance being sandwiched with a cathode and an anode, and an exciton is generated by an electron and a positive hole being injected into the emitting layer to be recombined, resulting emission utilizing light release (fluorescence•phosphorescence) at the time of deactivation of said exciton; the emission is possible at a voltage of approximately a few to a few tens volts, and an organic electroluminescent element is attracting attention with respect to such as superior viewing angle and high visual recognition due to a self-emission type as well as space saving and portability due to a completely solid element of a thin layer type.

However, in an organic electroluminescence in view of the future practical application, desired has been development of an organic EL element which efficiently emits at a high luminance with a low electric consumption.

In Japanese Patent No. 3093796, a slight amount of a fluorescent substance has been doped in a stilbene derivative, distyrylarylene derivative or a tristyrylarylene derivative, to achieve improved emission luminance and a prolonged lifetime of an element.

Further, there are known such as an element having an organic emitting layer comprising a 8-hydroxyquinoline aluminum complex as a host compound which is doped with a slight amount of a fluorescent substance (for example, JP-A 63-264692) and an element having an organic emitting layer comprising a 8-hydroxyquinoline aluminum complex as a host compound which is doped with quinacridone type dye (for example, JP-A 3-255190).

In the case of utilizing emission from an excited singlet as described above, since a generation ratio of a singlet exciton to a triplet exciton is 1/3, that is, a generation probability of an emitting exciton species is 25% and a light taking out efficiency is approximately 20%, the limit of an external quantum efficiency ($\square$ext) of taking out light is said to be 5%.

However, since an organic EL element which utilizes phosphorescence from an excited triplet has been reported from Princeton University (M. A. Baldo et al., Nature vol. 395, pp. 151-154 (1998)), researches on materials exhibiting phosphorescence at room temperature have come to be active.

For example, it is also disclosed in A. Baldo et al., Nature, vol. 403, No. 17, pp. 750-753 (2000), and U.S. Pat. No. 6,097,147.

Since the upper limit of internal quantum efficiency becomes 100% by utilization of an excited triplet, which is principally 4 times of the case of an excited singlet, it may be possible to achieve almost the same ability as a cooled cathode ray tube to attract attention also for an illumination application.

For example, in such as S. Lamansky et al., J. Am. Chem. Soc., vol. 123, p. 4304 (2001), many compounds mainly belonging to heavy metal complexes such as iridium complexes have been synthesized and studied.

Further, in the aforesaid, A. Baldo et al., Nature, vol. 403, No. 17, pp. 750-753 (2000), utilization of tris (2-phenylpyridine)iridium as a dopant has been studied.

In addition to these, M. E. Tompson et al., at The 10th International Workshops on Inorganic and Organic Electroluminescence (EL'00, Hamamatsu), have studied to utilize L2Ir(acac) such as (ppy)2Ir(acac) as a dopant, Moon-Jae Youn. Og., Tetsuo Tsutsui et al., also at The 10th International Workshops on Inorganic and Organic Electroluminescence (EL'00, Hamamatsu), have studied utilization of such as tris(2-(p-tolyl)pyridine)iridium (Ir(ptpy)3) and tris(benzo[h]quinoline)iridium (Ir(bzq)3) (herein, these metal complexes are generally referred to as orthometalated iridium complexes.).

Further, in also the aforesaid, S. Lamansky et al., J. Am. Chem. Soc., vol. 123, p. 4304 (2001), studies have been carried out to prepare an element utilizing various types of iridium complexes.

Further, to obtain high emission efficiency, Ikai et al., at The 10th International Workshops on Inorganic and Organic Electroluminescence (EL'00, Hamamatsu) utilized a hole transporting compound as a host of a phosphorescent compound. Further, M. E. Tompson et al. utilized various types of electron transporting materials as a host of a phosphorescent compound doped with a new iridium complex. An orthometalated complex provided with platinum instead of iridium as a center metal is also attracting attention. With respect to these types of complexes, many examples having a characteristic ligand are known (for example, refer to Patent Documents 1-5 and Non-Patent Document 1.).

In any case, emission luminance and emission efficiency are significantly improved compared to conventional elements because the emitting light arises from phosphorescence, however, there has been a problem of a poor emission lifetime of the element compared to conventional elements. It is hard to achieve an emission of a short wavelength and an improvement of an emission lifetime of the element for a phosphorescent emission material provided with a high efficiency. At present state, it cannot be achieved a level of a practical use.

In order to improve the above-described defects, there are known an Ir complex and a Pt complex having a phenylimidazole ligand (for example, refer to Patent Documents 6-7). However, the emission efficiency and the emission lifetime are still not fully satisfied, and further improvement in emission efficiency and emission lifetime are demanded.

[Patent Document 1] JP-A 2002-332291
[Patent Document 2] JP-A 2002-332292
[Patent Document 3] JP-A 2002-338588
[Patent Document 4] JP-A 2002-226495
[Patent Document 5] JP-A 2002-234894
[Patent Document 6] WO 02/15645
[Patent Document 7] WO 05/7767

DISCLOSURE OF THE INVENTION

Problems to be Solved by the Invention

An object of the present invention is to provide an organic EL element material which has high emission efficiency and long emission lifetime, a lighting device and a display device.

Means to Solve the Problems

An object of the present invention described above has been achieved by the following constitutions. 1. An organic electroluminescent element comprising a substrate having thereon at least an anode and a cathode, and a light emitting layer between the aforesaid anode and the aforesaid cathode, wherein at least one light emitting layer incorporates a compound represented by Formula (A):

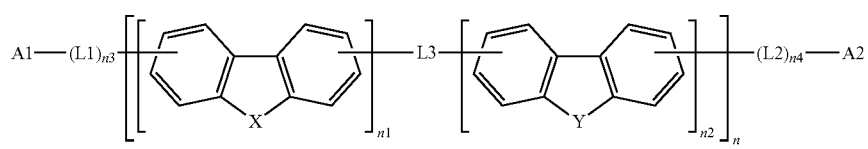

Formula (A)

wherein A1 and A2 each represents a hydrogen atom or a substituent, provided that at least one of A1 and A2 is a substituent; X and Y each represents O, S, Se, Te, or N—R (where R represents a hydrogen atom or a substituent); L1, L2, and L3 each represents a divalent linking group; n represents an integer of at least 1; n1 and n2 each represents an integer of at least 0; and n3 and n4 each represents 0 or 1, provided that the following condition is satisfied, $n1+n2 \geq 2$.

2. The organic electroluminescent element, described in the above-mentioned item 1, wherein the aforesaid L3 represents an arylene group, a heteroarylene group, a divalent heterocyclic group or an alkylene group.

3. The organic electroluminescent element, described in the above-mentioned item 1, wherein the aforesaid L3 represents an arylene group.

4. The organic electroluminescent element, described in the above-mentioned item 1, wherein the aforesaid L3 represents a m-phenylene group.

5. The organic electroluminescent element, described in any one of the above-mentioned items 1-4, wherein the aforesaid n1 represents 1 or 2.

6. The organic electroluminescent element, described in any one of the above-mentioned items 1-5, wherein the aforesaid n2 represents 1 or 2.

7. The organic electroluminescent element, described in any one of the above-mentioned items 1-6, wherein the aforesaid n represents 1 or 2.

8. The organic electroluminescent element, described in any one of the above-mentioned items 1-7, wherein at least one of the aforesaid A1 and A2 represents a nitrogen atom-containing substituent.

9. The organic electroluminescent element, described in the above-mentioned item 8, wherein the aforesaid nitrogen atom-containing substituent is a carbazolyl group.

10. The organic electroluminescent element, described in the above-mentioned item 8, wherein the aforesaid nitrogen atom-containing substituent represents a carbolynyl group and the aforesaid carbolynyl group is the substituent which is derived from the carboline derivative represented by Formula (a):

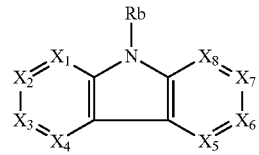

Formula (a)

wherein X1-X8 each represents a nitrogen atom or —C(Ra)=; at least one of the aforesaid X1-X8 represents a nitrogen atom; and Ra and Rb each represents a hydrogen atom or a substituent.

11. The organic electroluminescent element, described in the above-mentioned item 8, wherein the aforesaid nitrogen atom-containing substituent is a diarylamino group.

12. The organic electroluminescent element, described in any one of the above-mentioned items 1-11, wherein the aforesaid X is an oxygen atom.

13. The organic electroluminescent element, described in any one of the above-mentioned items 1-12, wherein the aforesaid light emitting layer incorporates a phosphorescence emitting metal complex.

14. The organic electroluminescent element, described in the above-mentioned item 13, wherein the aforesaid phosphorescence emitting metal complex is an Ir complex.

15. The organic electroluminescent element, described in the above-mentioned items 13 or 14, wherein the aforesaid phosphorescence emitting metal complex is represented by Formula (B):

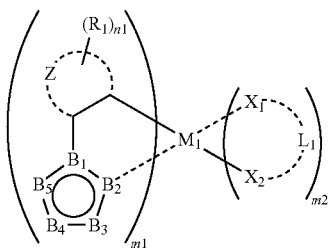

Formula (B)

wherein R1 represents a substituent; Z represents a group of metal atoms necessary for forming a 5-7 membered ring; n1 represents an integer of 0-5; B1-B5 each represents a carbon atom, a nitrogen atom, an oxygen atom, or a sulfur atom and at least one represents a nitrogen atom; M1 represents a metal of Groups 8-10 in the element periodic table; X1 and X2 each represents a carbon atom, a nitrogen atom, or an oxygen atom; L1 represents a group of atoms which form a bidentate ligand with X1 and X2; m1 represents 1, 2, or 3; and m2 represents 0, 1, or 2, provided that a sum of m1 and m2 is 2 or 3.

16. The organic electroluminescent element, described in any one of the above-mentioned items 1-15, wherein m2 of the phosphorescence emitting metal complex represented by the aforesaid Formula (B) is 0.
17. The organic electroluminescent element, described in the above-mentioned items 15 or 16, wherein a nitrogen-containing heterocyclic ring formed by phosphorescence emitting metal complexes B1-B5 represented by the aforesaid Formula (B) is an imidazole ring.
18. The organic electroluminescent element, described in any one of the above-mentioned items 1-17, emitting white light.
19. A display device provided with the organic electroluminescent element described in any one of the above-mentioned items 1-18.
20. An illuminating device provided with the organic electroluminescent element described in any one of the above-mentioned items 1-18.

Effects of the Invention

The present invention has enabled to provide an organic EL element, a lighting device and a display device having high emission efficiency and long emission lifetime.

Figure 1:
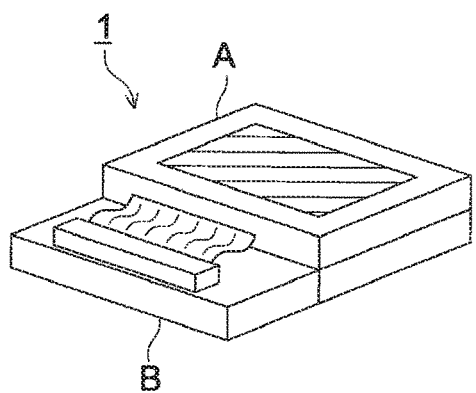
FIG. 1 is a schematic drawing to show an example of a display device constituted of an organic EL element.

DESCRIPTION OF SYMBOLS 1 display
3 pixel
5 scanning line
6 data line
A display section
B control section
101 organic EL element
107 glass substrate having a transparent electrode
106 organic EL layer
105 cathode
102 glass cover
108 nitrogen gas
109 desiccant

BEST MODES TO CARRY OUT THE INVENTION

In the organic EL element of the present invention, by using any one of the aforementioned embodiments of items 1-18, there has been provided an organic EL element exhibiting high emission taking out quantum efficiency and having a prolonged emission lifetime. And further, a lighting equipment and a display device pf high luminance can be successfully provided.

Each of the constituent elements of the present invention will now be detailed successively.

<Constituting Layers of Organic EL Element>

Specific examples of a preferable layer constitution of an organic EL element of the present invention are shown below; however, the present invention is not limited thereto.
(i) anode/light emitting layer/electron transport layer/cathode
(ii) anode/positive hole transport layer/light emitting layer/electron transport layer/cathode
(iii) anode/positive hole transport layer/light emitting layer/positive hole inhibition layer/electron transport layer/cathode
(iv) anode/positive hole transport layer/light emitting layer/positive hole inhibition layer/electron transport layer/cathode buffer layer/cathode
(v) anode/anode buffer layer/positive hole transport layer/light emitting layer/positive hole inhibition layer/electron transport layer/cathode buffer layer/cathode In the organic EL element of the present invention, the maximum wavelength of light emitted from the blue light emitting layer is preferably within 430-480 nm, and the green light emitting layer is preferably a monochromatic light emitting layer which results in the maximum wavelength of the emitted light within 510-550 nm, while the red light emitting layer is a monochromatic light emitting layer which results in the maximum wavelength of the emitted light in the range of 600-640 nm. Display devices employing these are preferred. Further, a while light emitting layer is acceptable, which is prepared by laminating at least three of these layers. Further, between the light emitting layers may be present a non-light emitting intermediate layer. As the organic EL element of the present invention, preferred is a white light emitting layer, and illuminating devices employing these are preferred.

Each of the layers which constitute the organic EL elements of the present invention will now be sequentially detailed.

<Emitting Layer>

The emitting layer of the present invention is a layer, which emits light via recombination of electrons and positive holes injected from an electrode or a layer such as an electron transport layer or a positive hole transport layer. The emission portion may be present either within the emitting layer or at the interface between the emitting layer and an adjacent layer thereof.

The total thickness of the light emitting layer is not particularly limited. However, in view of the layer homogeneity, the minimization of application of unnecessary high voltage during light emission, and the stability enhancement of the emitted light color against the drive electric current, the layer thickness is regulated preferably in the range of 2 nm-5 μm, more preferably in the range of 2 nm-200 nm, but most preferably in the range of 10-20 nm.

With regard to preparation of the light emitting layer, light emitting dopants and host compounds, described below, may be subjected to film formation via a conventional thin filming method such as a vacuum deposition method, a spin coating method, a casting method, an LB method, or an ink-jet method.

It is preferable that the light emitting layer of the organic EL element of the present invention incorporates host compounds and at least one kind of light emitting dopants (also referred to as phosphorescence dopants or phosphorescence emitting dopants) and fluorescence dopants.

(Host Compounds (Also Referred to as Light Emitting Hosts)

Host compounds employed in the present invention will now be described.

"Host compounds", as described in the present invention, are defined as compounds, incorporated in a light emitting layer, which result in a weight ratio of at least 20% in the above layer and also result in a phosphorescent quantum yield of the phosphorescence emission of less than 0.1. Further, of compounds incorporated in the light emitting layer, it is preferable that the weight ratio in the aforesaid layer is at least 20%.

<<Compounds Represented by Formula (A)>>

Compounds represented by Formula (A) will be described.

Compounds represented by Formula (A) according to the present invention are incorporated in the light emitting layer of the organic EL element of the present invention. It is preferable that the compounds represented by the aforesaid Formula (A) are employed as a host compound in the light emitting layer.

In Formula (A), examples of the substituents represented by A1 and A2 each include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group, an allyl group, a 1-propenyl group, a 2-butenyl group, a 1,3-butadienyl group, a 2-pentenyl group, and an isopropenyl group); an alkynyl group (for example, an ethynyl group and a propargyl group); an aromatic hydrocarbon ring group (also called an aromatic carbon ring or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyryl group); an aromatic heterocyclic group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolynyl group; a diazacarbazolyl group (which is a group in which one of the carbon atoms constituting the carboline ring of the above carbolynyl group is replaced with a nitrogen atom), a phtharadinyl group; a heterocyclic group (for example, a pyrrolidyl group, an imidazolidyl group, a morpholyl group, and an oxazilidyl group); an alkoxyl group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-oyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group, an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a cyano group; a nitro group; a hydroxyl group; a mercapto group; a silyl group (for example, a trimethylsilyl group, a triisopropylsilyl group, a triphenylsilyl group, and a phenyldiethylsilyl group), and a phosphono group.

These substituents may further be substituted with the aforesaid substituents. Further, a plurality of these substituents may mutually be joined to form a ring.

Of these, it is preferable that in Formula (A), at least one of substituents represented by each of A1 and A2 in Formula (A) is a nitrogen atom-containing substituent. Further, as the nitrogen atom-containing substituent, preferred are a carbazolyl group, a carbolynyl group, and a diarylamino group.

The aforesaid carbolynyl group is a group derived from the carboline derivative represented by the aforesaid Formula (a), and in Formula (a), the substituent represented by Ra or Rb is as defined for the substituent represented by each of A1 and A2 in Formula (A).

Aryl of the diarylamino group is as defined for the substituent represented by each of A1 and A2 in Formula (A).

In N—R represented by X and Y of Formula (A), the substituent represented by R is as defined for the substituent represented by each of A1 and A2. Examples of preferably employed ones include an alkyl group, an alkenyl group, an alkynyl group, an aromatic hydrocarbon group, an aromatic heterocyclic group, a heterocyclic group, an alkoxycarbonyl group, an aryloxycarbonyl group, an acyl group, a carbamoyl group, and a fluorinated hydrocarbon group. Specific examples of the substituents are the same as those represented by each of above A1 and A2.

In Formula (A), divalent linking groups represented by each of L1, L2, and L3 include an alkylene group (for example, an ethylene group, a trimethylene group, a tetramethylene group, a propylene group, an ethylethylene group, a pentamethylene group, and a hexamethylene group), an alkenylene group (for example, a vinylene group, a propenylene group, a butenylene group, a pentenylene group, a 1-methylvinylene group, a 1-methylpropenylene group, a 2-methylpropenylene group, a 1-methylpentenylene group, a 3-methylpentenylene group, a 1-ethylvinylene group, a 1-ethylpropenylene group, a 1-ethylbutenylene group, and a 3-ethylbutenylene group), an alkynylene group (for example, an ethynylene group, a 1-propynylene group, a 1-butynylene group, a 1-pentynylene group, a 1-hexnylene group, a 2-butynylene group, a 2-pentynylene group, a 1-methylethynylene group, a 3-methyl-1-propynylene group, and a 3-methyl-1-butynylene group), an arylene group (for example, an o-phenylene group, a m-phenylene group, a p-phenylene group, a naphthalenediyl group, an anthracenediyl group, a naphthacenediyl group, a pyrenediyl group, a naphthylnaphthalenediyl group, a biphenyldiyl group (for example, a [1,1'-biphenyl]-4,4'-diyl group and a 3,3'-biphenyldiyl group, and a 3, 6-biphenyldiyl group), terphenyldiyl group, quaterphenyldiyl group, a quinquephenyldiyl group, a sexiphenyldiyl group, a septiphenyldiyl group, an octiphenyldiyl group, a nobiphenyldiyl group, and a deciphenyldiyl group), a heteroarylene group (for example, a divalent group derived from the group consisting of a carbazole group, a carboline ring, a diazacarbazole ring (also referred to as a monoazacarboline group, indicating a ring structure formed in such a manner that one of the carbon atoms constituting the carboline ring is replaced with a nitrogen atom), a triazole ring, a pyrrole ring, a pyridine ring, a pyrazine ring, a quinoxaline ring, a thiophene ring, an oxadiazole ring, a dibenzofuran ring, a dibenzothiophene ring and an indole ring), and a divalent heterocyclic group (for example, a divalent group derived from a pyrrolidine ring, a imidazolidine ring, a morpholine ring, and a oxazolidine ring), and a chalcogen atom such as oxygen and sulfur.

Further, employed may be a group which links via a hetero atom such as in an alkylimino group, a dialkylsilanediyl group, or a diarylgermandiyl group.

Still further, as the aforesaid L3, preferred are an arylene group, a heteroarylene group, a divalent heterocyclic group, and an alkylene group. Of these, more preferred is the arylene group and most preferred is the m-phenylene group.

Specific examples of the phosphorescent compounds represented by Formula (A) of the present invention will now be listed, however the present invention is not limited thereto.

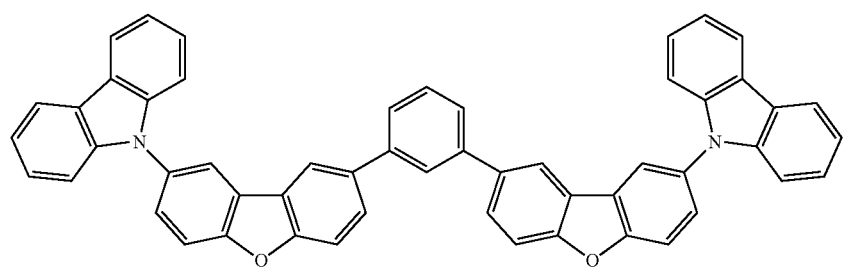

(1)

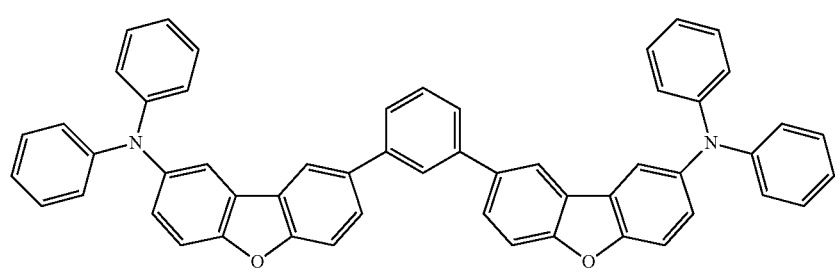

(2)

-continued
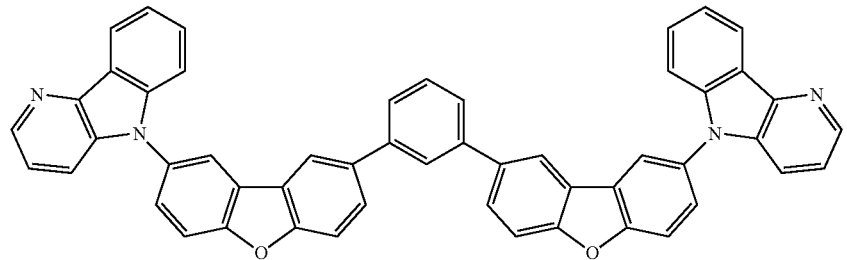
(3)
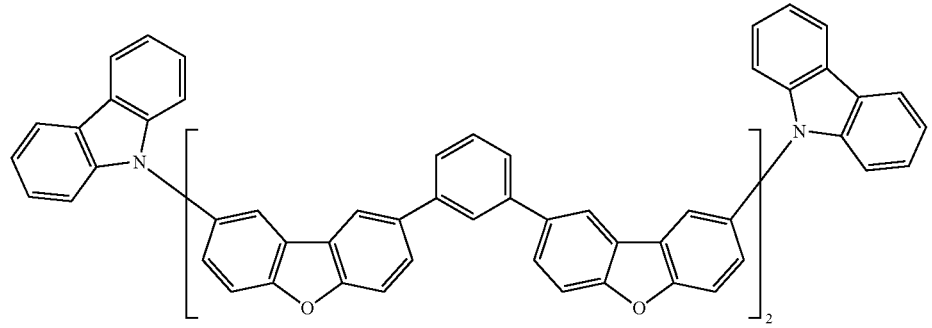
(4)
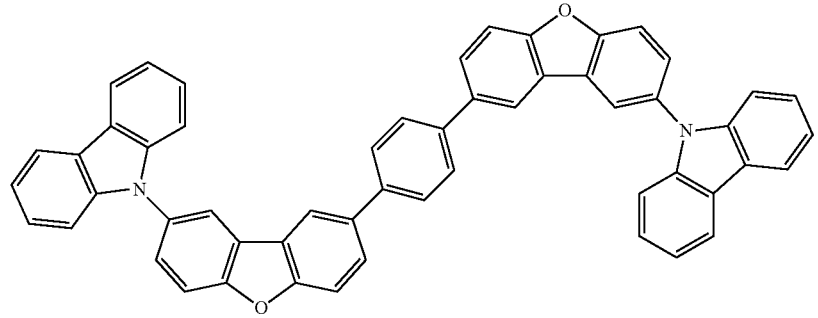
(5)
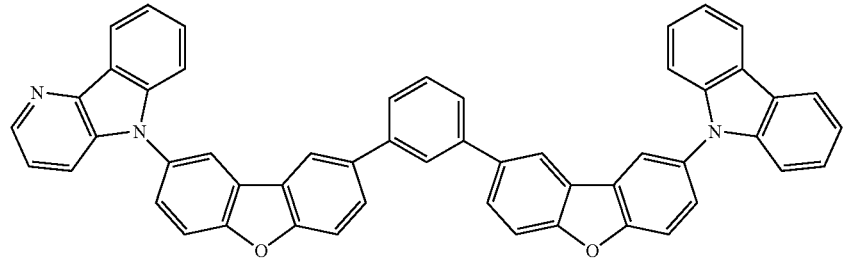
(6)
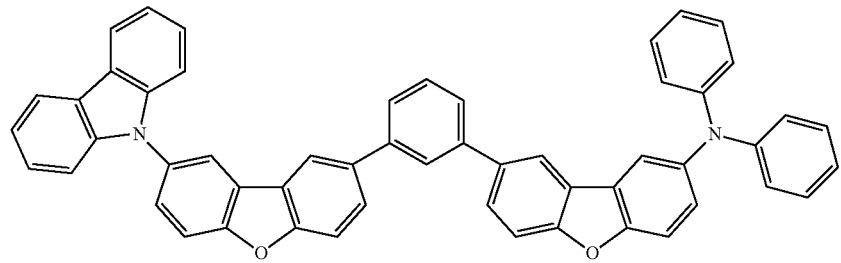
(7)

-continued
(8)
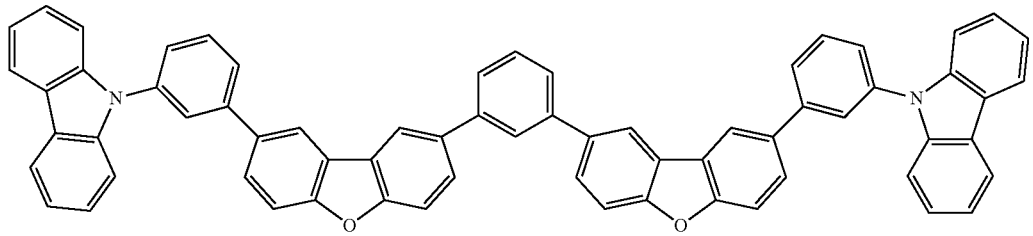
(9)
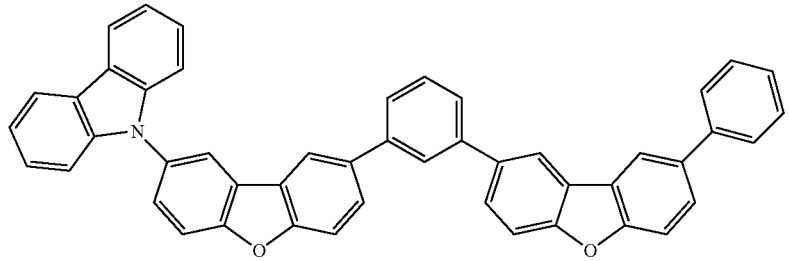
(10)
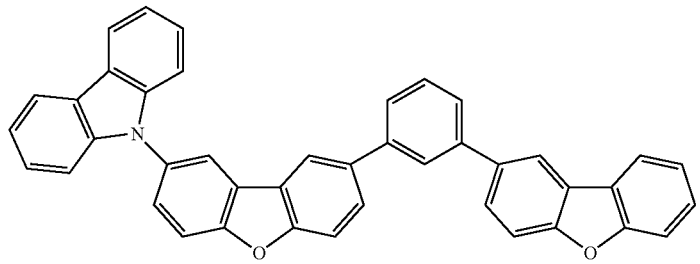
(11)
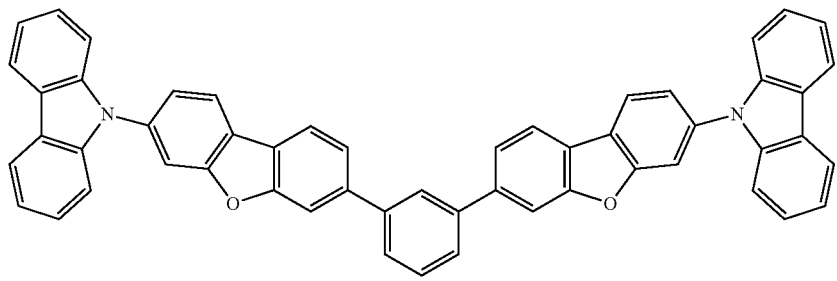
(12)
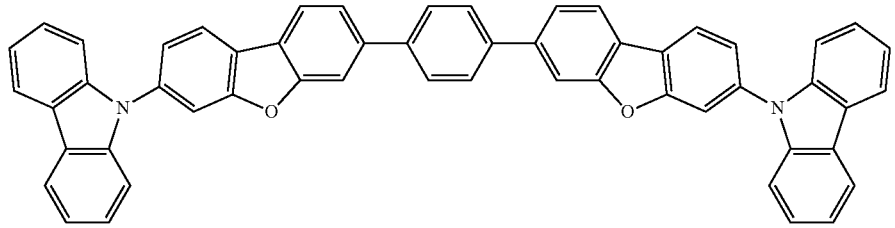
(13)
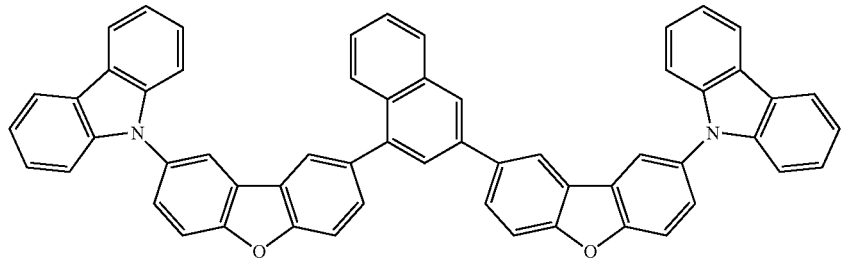

-continued
(14)
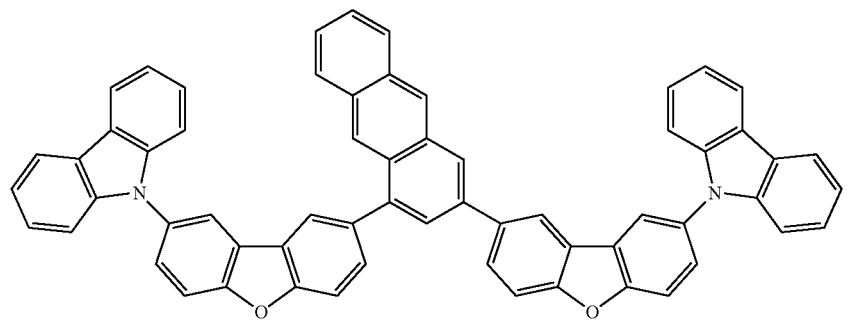
(15)
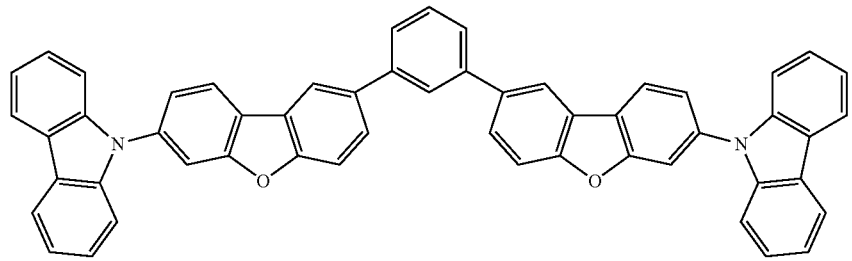
(16)
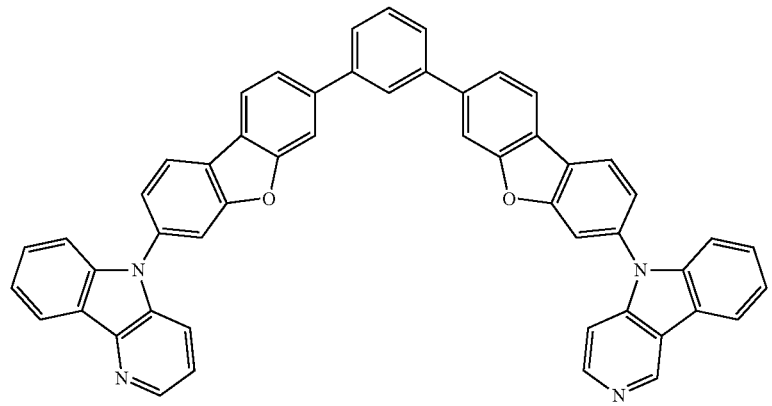
(17)
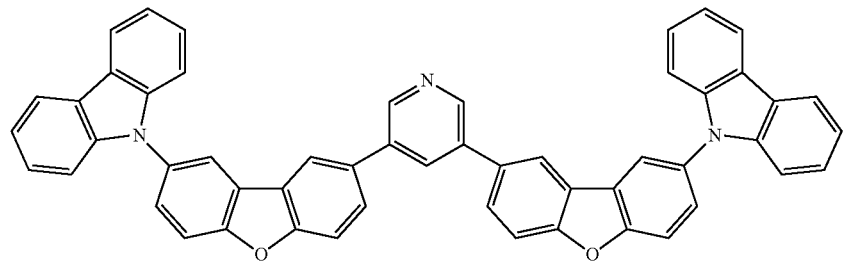
(18)
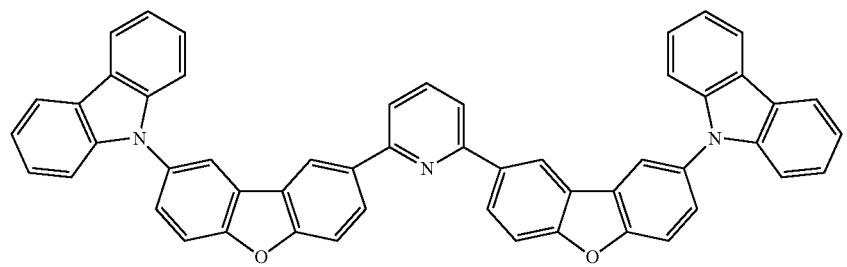

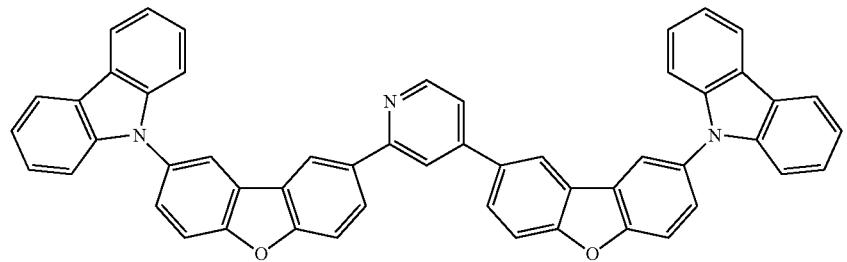
(19)
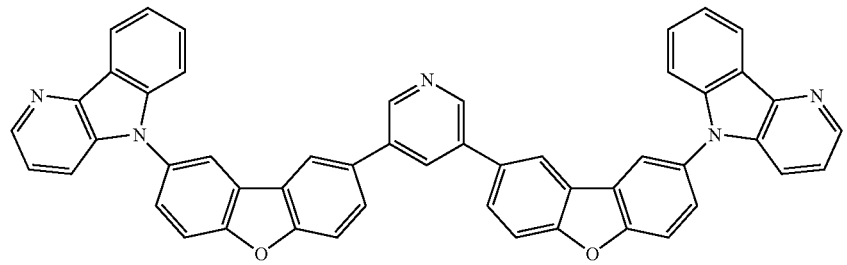
(20)
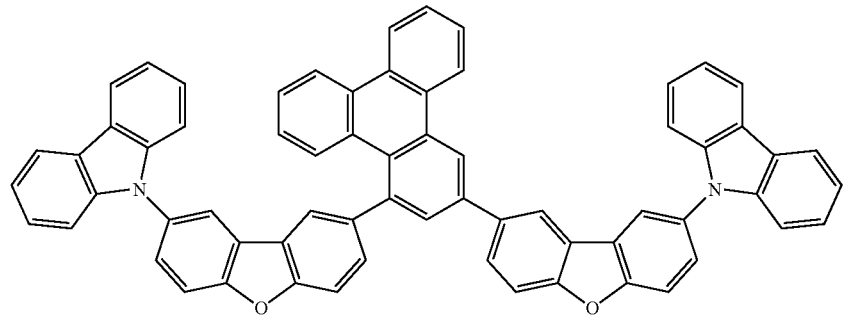
(21)
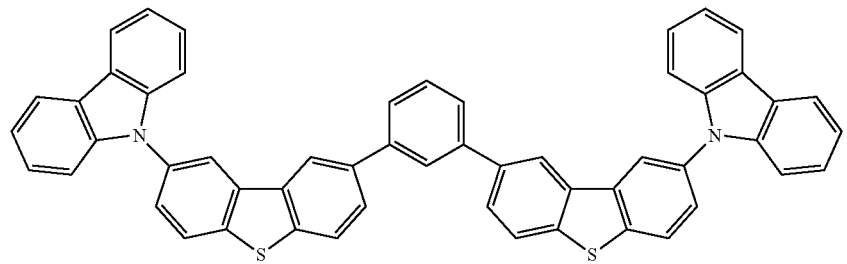
(22)
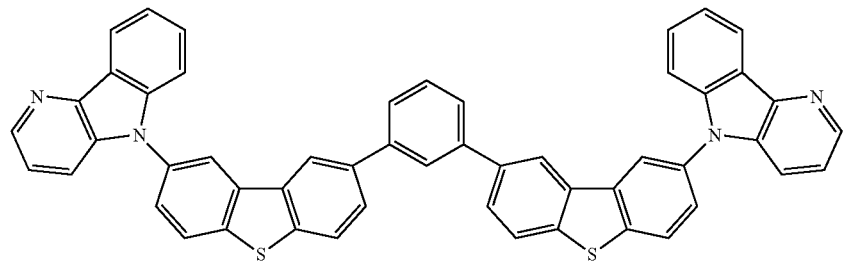
(23)

-continued
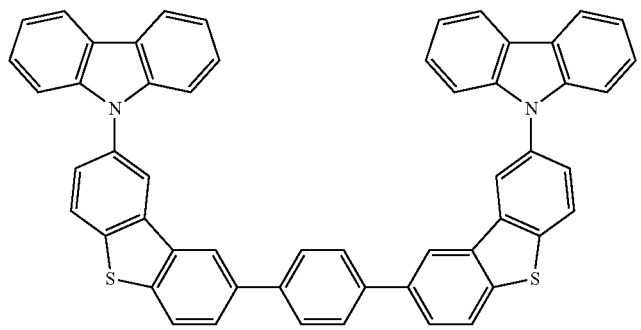
(24)
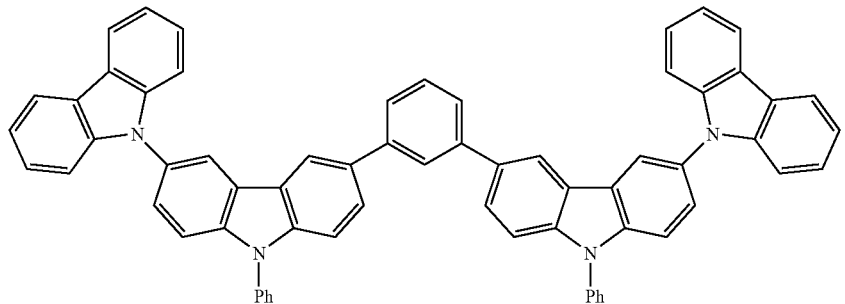
(25)
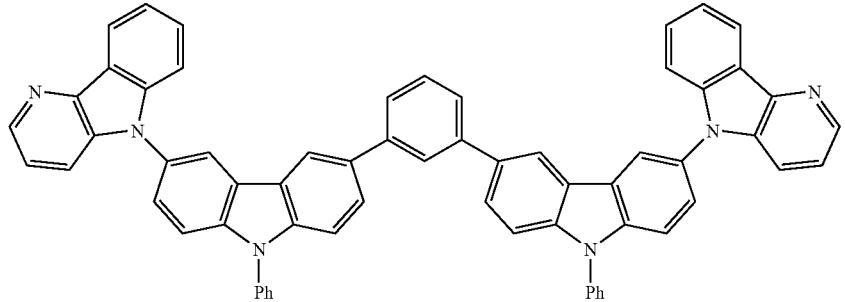
(26)
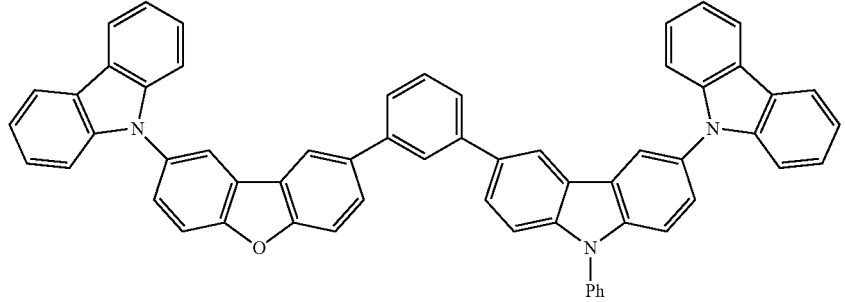
(27)
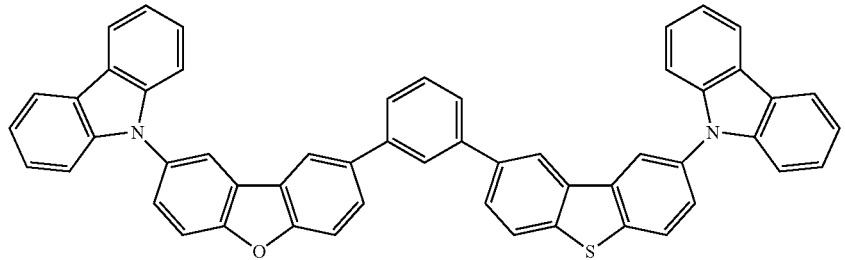
(28)

-continued
(29)
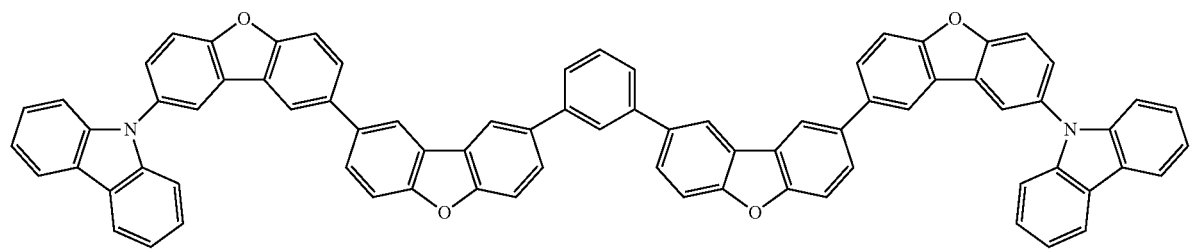
(30)
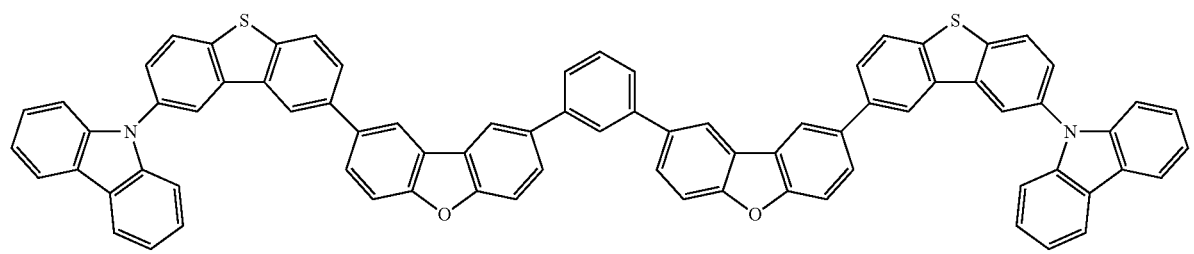
(31)
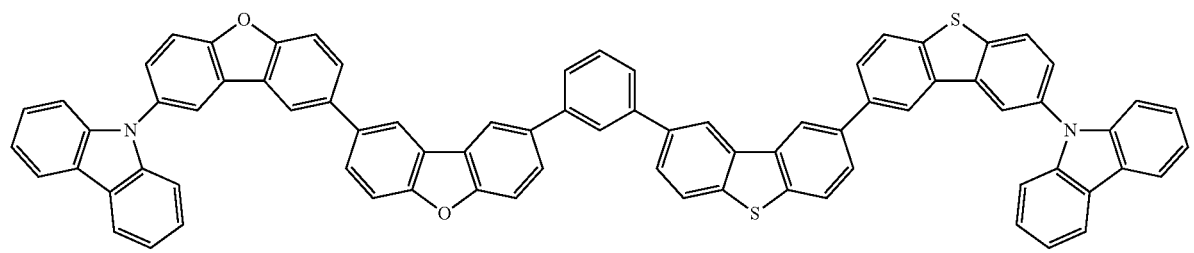
(32)
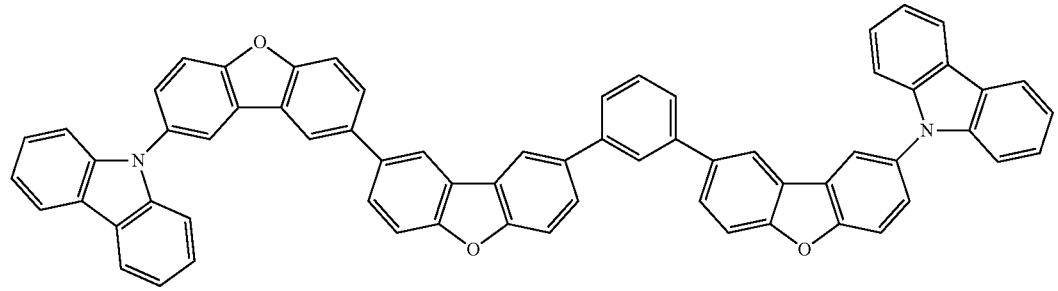
(33)
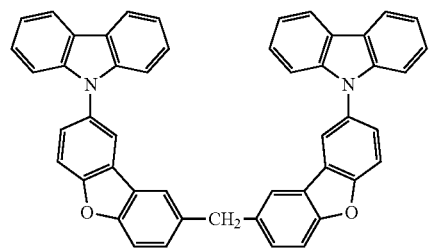
(34)
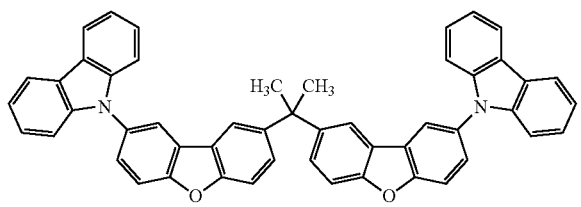

-continued
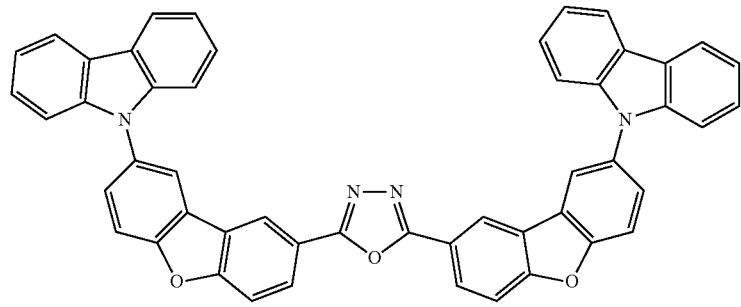
(35)
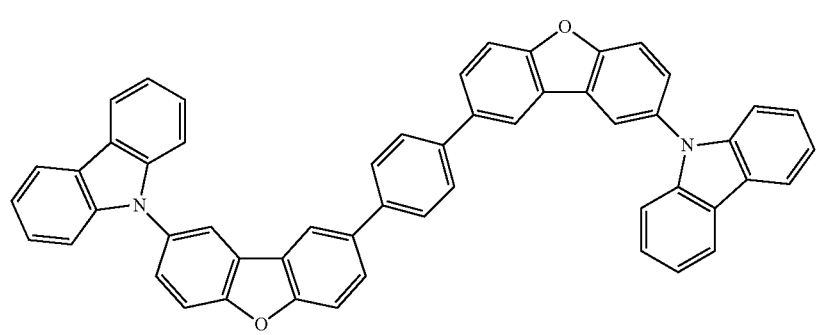
(36)
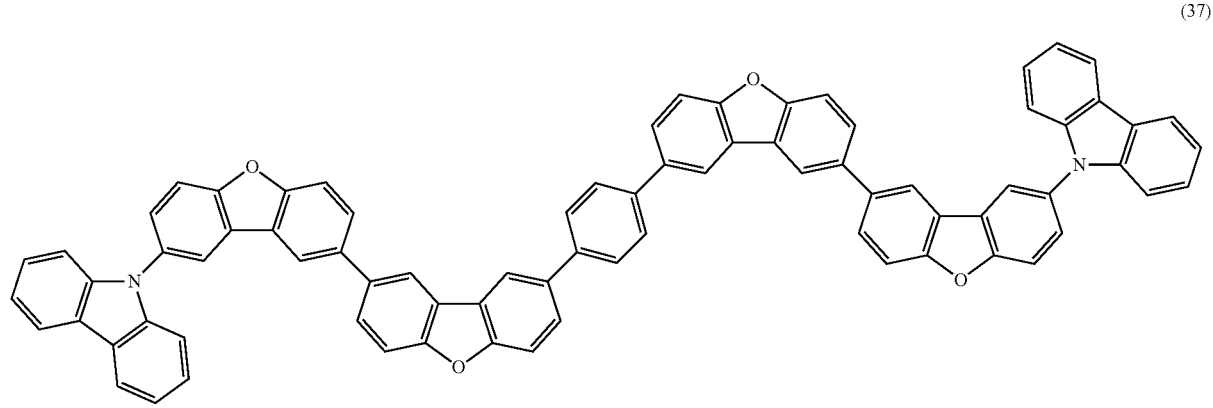
(37)
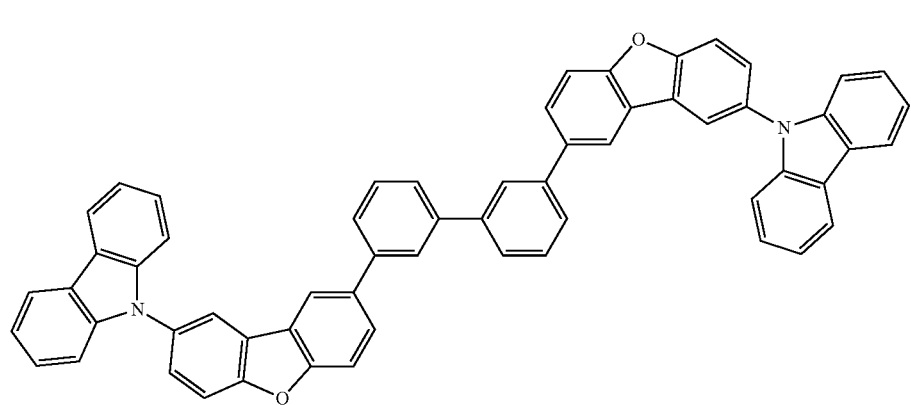
(38)

-continued
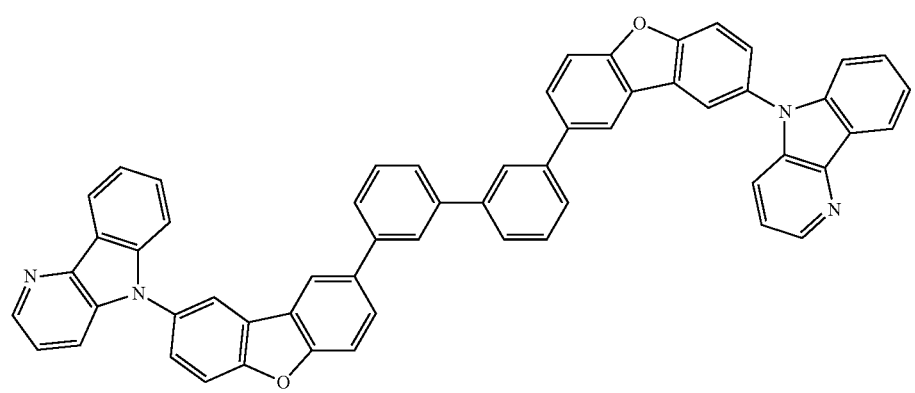
(39)
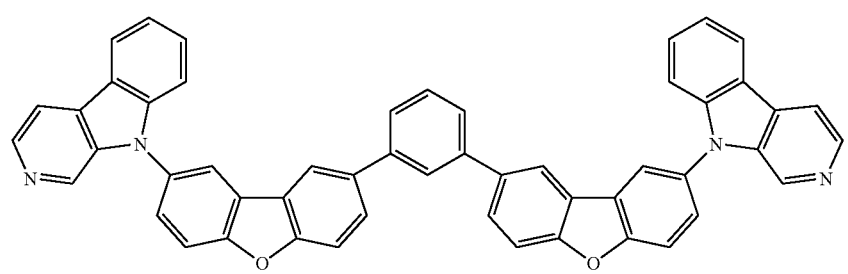
(40)
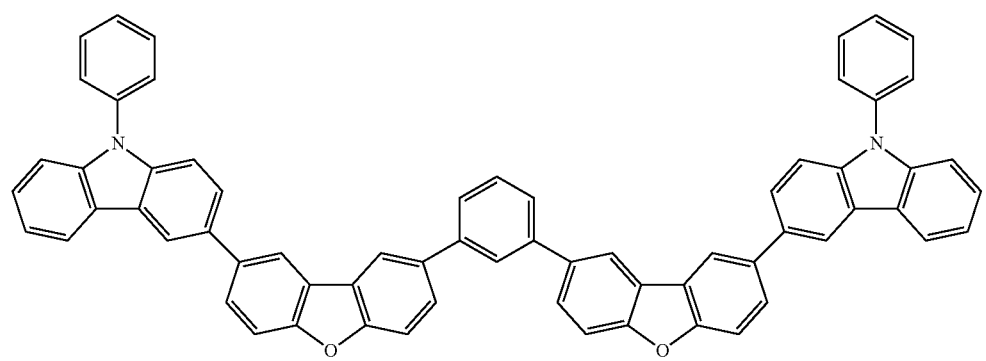
(41)
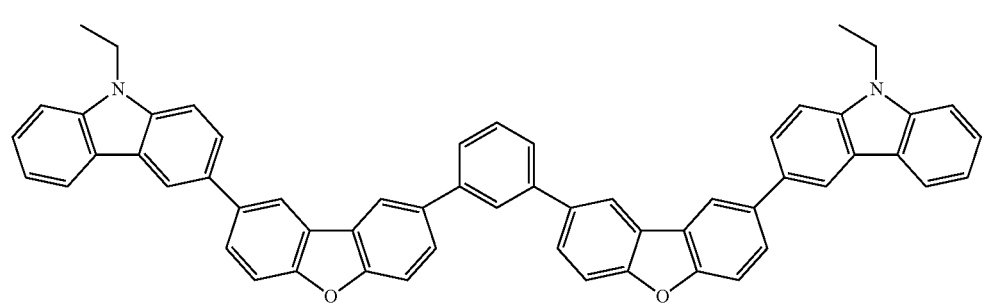
(42)

-continued

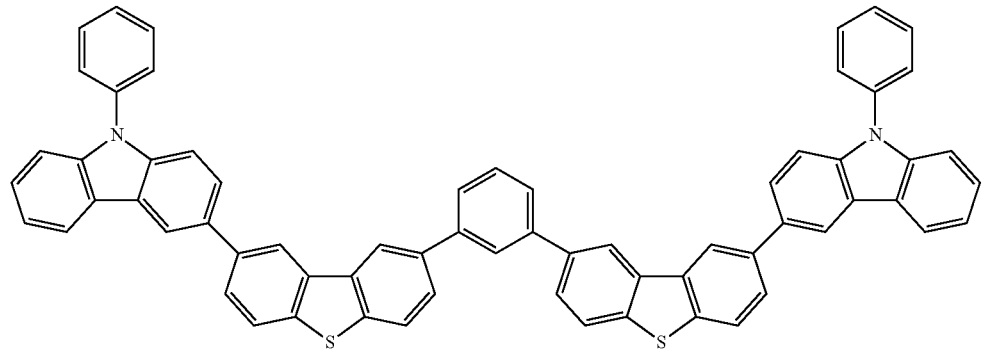

(43)

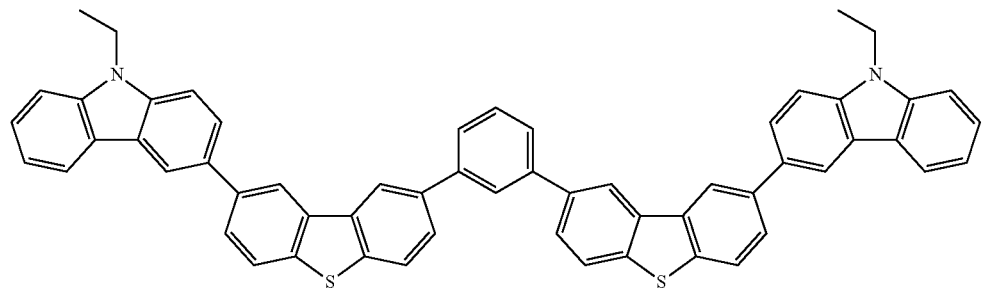

(44)

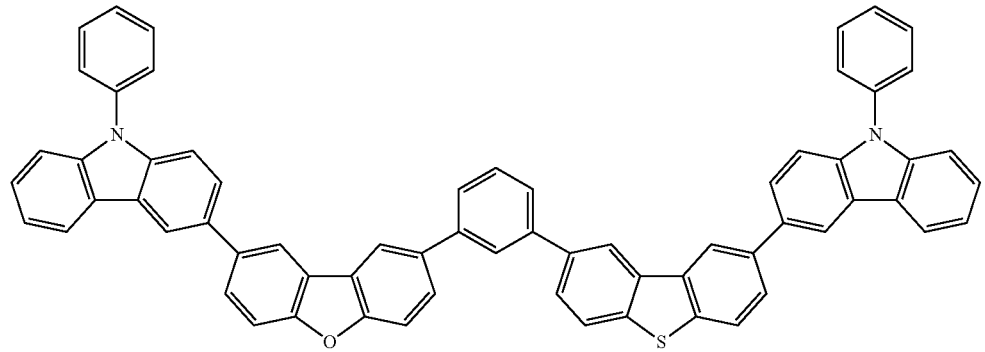

(45)

Synthesis of compounds represented by Formula (A) according to the present invention may be carried out based on the method known in the prior art or via referring to literatures (for example, conventional literatures which are described in the host compounds below).

An emission host compound of the present invention may be used with plural known host compounds. It is possible to control the transfer of charges by making use of a plurality of host compounds, which results in high efficiency of an organic EL element. In addition, it is possible to mix a different emission lights by making use of a plurality of emission dopants that will be described later. Any required emission color can be obtained thereby.

Further, an emission host of the present invention may be either a low molecular weight compound or a polymer compound having a repeating unit, in addition to a low molecular weight compound provided with a polymerizing group such as a vinyl group and an epoxy group (an evaporation polymerizing emission host).

A known emission host which may be jointly used is preferably a compound having a positive hole transporting ability and an electron transporting ability, as well as preventing elongation of an emission wavelength and having a high Tg (a glass transition temperature).

As specific examples of an emission host compounds described in the following Documents are preferable.

For example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

(Emission Dopant)

The emission dopant of the present invention will now be described.

As light emitting dopants according to the present invention, employed may be fluorescent dopants (also referred to as fluorescent compounds), phosphorescence emitting dopants (also referred to as phosphorescent dopants, phosphorescent compounds, phosphorescence emitting compounds, or phosphorescent dopants). However, in view of production of organic EL elements exhibiting higher light emission efficiency, as light emitting dopants (also referred simply to as light emitting materials) employed in the light emitting layer of the organic EL element and light emitting units in the present invention, it is preferable to simultaneously incorporate the aforesaid host compounds and the phosphorescence emitting dopants.

(Phosphorescence-Emitting Dopant)

A phosphorescence-emitting dopant of the present invention will be described.

The phosphorescence-emitting dopant of the present invention is a compound, wherein emission from an excited triplet state thereof is observed, specifically, emitting phosphorescence at room temperature (25° C.) and exhibiting a phosphorescence quantum yield of at least 0.01 at 25° C. The phosphorescence quantum yield is preferably at least 0.1.

The phosphorescence quantum yield can be determined via a method described in page 398 of Bunko II of Dai 4 Han Jikken Kagaku Koza 7 (Spectroscopy II of 4th Edition Lecture of Experimental Chemistry 7) (1992, published by Maruzen Co., Ltd.). The phosphorescence quantum yield in a solution can be determined using appropriate solvents. However, it is only necessary for the phosphorescence-emitting dopant of the present invention to exhibit the above phosphorescence quantum yield using any of the appropriate solvents.

Two kinds of principles regarding emission of a phosphorescence-emitting dopant are cited. One is an energy transfer-type, wherein carriers recombine on a host compound on which the carriers are transferred to produce an excited state of the host compound, and then via transfer of this energy to a phosphorescence-emitting dopant, emission from the phosphorescence-emitting dopant is realized. The other is a carrier trap-type, wherein a phosphorescence-emitting dopant serves as a carrier trap and then carriers recombine on the phosphorescence-emitting dopant to generate emission from the phosphorescence-emitting dopant. In each case, the excited state energy of the phosphorescence-emitting dopant is required to be lower than that of the host compound.

<<Compounds Represented by Formula (B)>>

Compounds represented by Formula (B) will now be described.

As phosphorescence emitting metal complexes according to the present invention, preferably employed are compounds represented by the aforesaid Formula (B).

In Formula (B), substituents represented by R1 are as defined for substituents represented by each of A1 and A2 in Formula (A). Of these substituents, preferred is an alkyl group or an aryl group, and more preferred is an unsubstituted alkyl group or aryl group.

In formula (B), examples as a 5- to 7-membered ring formed by Z include a benzene ring, a naphthalene ring, a pyridine ring, a pyrimidine ring, a pyrrole ring, a thiophene ring, a pyrazole ring, an imidazole ring, an oxazole ring, and a thiazole ring. Of these, preferred is the benzene ring.

In Formula (B), B1-B5 each represents a carbon atom, a nitrogen atom, an oxygen atom, or a sulfur atom, and at least one of them represents a nitrogen atom. The ring formed by the aforesaid B1-B5 represents an aromatic heterocyclic ring having at least one nitrogen atom.

In Formula (B), examples of aromatic heterocyclic rings having at least one nitrogen atom, which are formed via B1-B5, include a pyrrole ring, a pyrazole ring, an imidazole ring, a triazole ring, a tetrazole ring, an oxazole ring, an isooxazole ring, a thiazole ring, an isothiazole ring, an oxadiazole ring, and a thiadiazole ring. Of these, preferred are the pyrazole ring and the imidazole ring, and particularly preferred is the imidazole ring.

These rings may be further substituted with the substituent represented by the aforesaid R1. Preferred substituents include an unsubstituted alkyl group and an unsubstituted aryl group.

Specific examples of bidentate ligands represented by X1-L1-X2 in Formula (B) include phenylpyridine, phenylpyrazole, phenylimidazole, phenyltriazole, phenyltetrazole, pyrazabole, picolinic acid, and acetylacetone. Further, these ligands may further be substituted with the substituent represented by the aforesaid R1.

"m1" represents an integer of 1, 2, or 3, and m2 represents an integer of 0, 1, or 2, while m1+m2 is 2 or 3. In these cases, a case is preferred in which m2 is 0.

As metals (including the case of metal ions) represented by M1 in Formula (B), employed are transition metal elements (also referred simply to as transition metals) of Groups 8-10 in the element periodic table. Of these, preferred are iridium and platinum, while iridium is more preferred.

Incidentally, phosphorescence emitting metal complexes, represented by Formula (B), may or may not incorporate polymerizable groups or reactive groups.

Specific examples of phosphorescence emitting metal complexes, represented by formula (B), are listed below, however the present invention is not limited thereto.

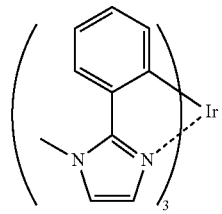

1-1

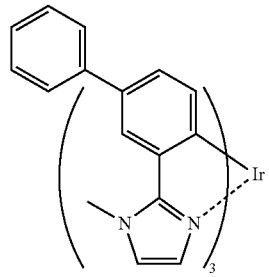

1-2

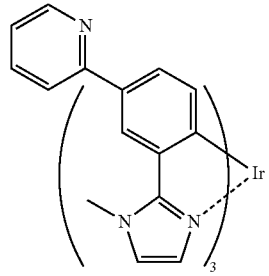

1-3

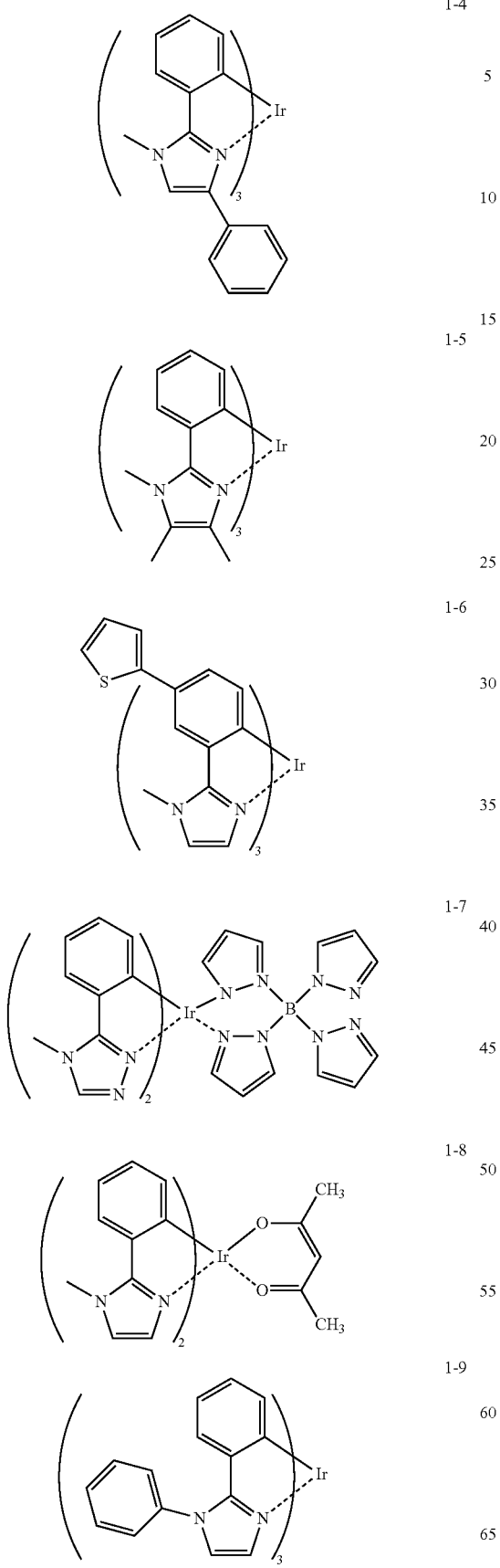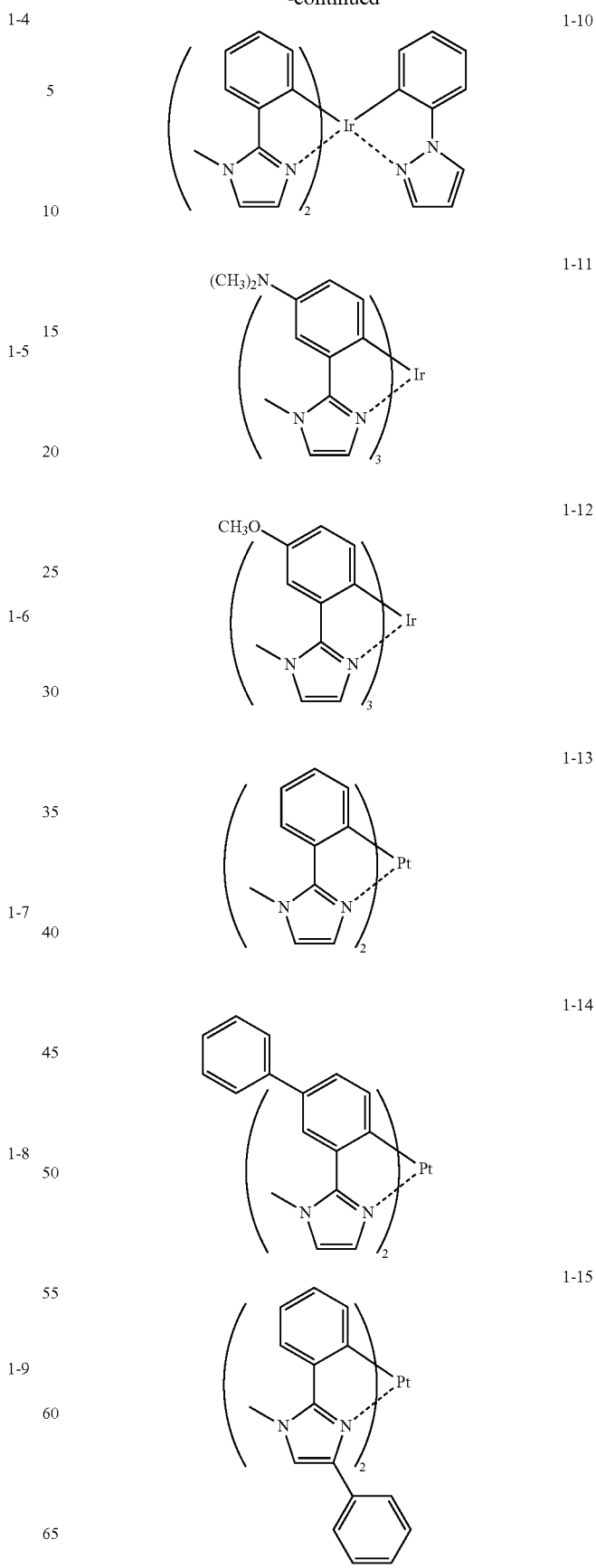

1-16
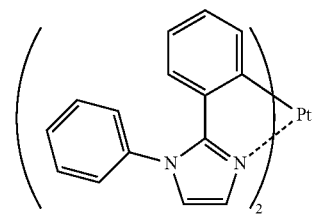
1-17
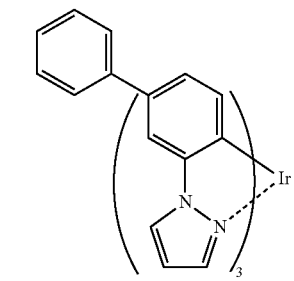
1-18
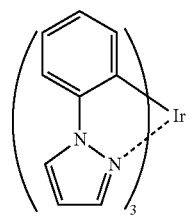
1-19
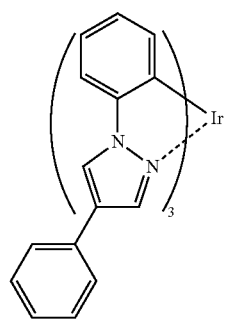
1-20
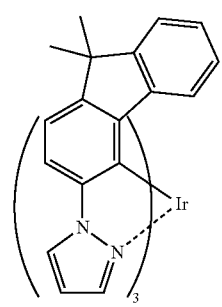
1-21
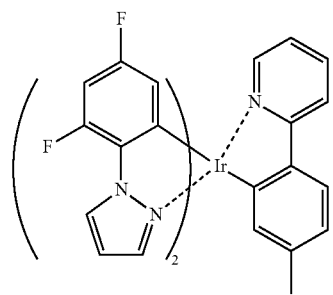
1-22
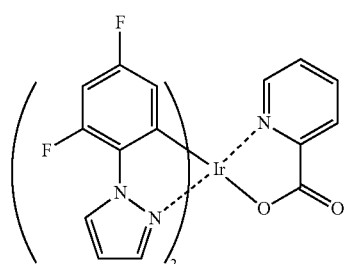
1-23
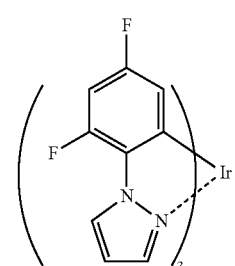
1-24
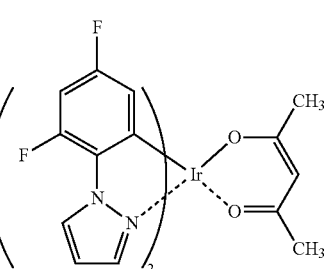
1-25
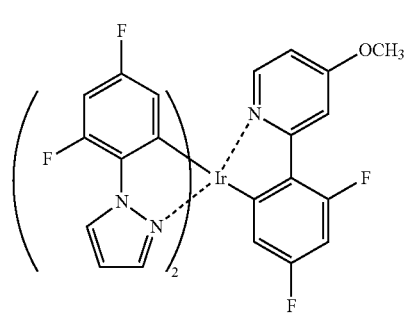
1-26

1-27
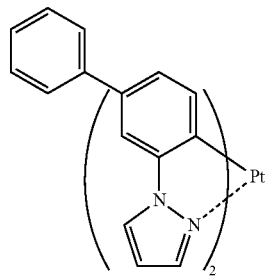
1-28
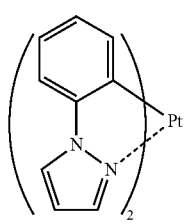
1-29
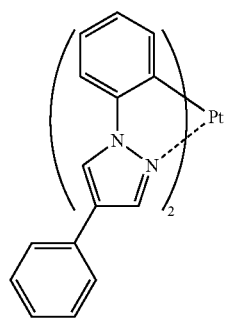
1-30
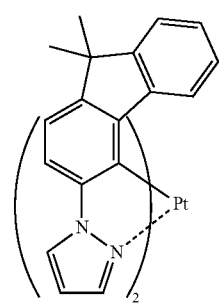
1-31
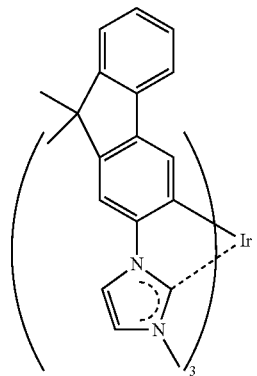
1-32
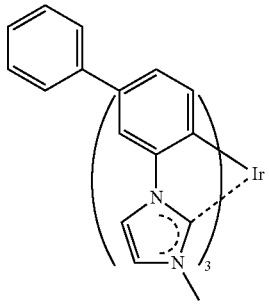
1-33
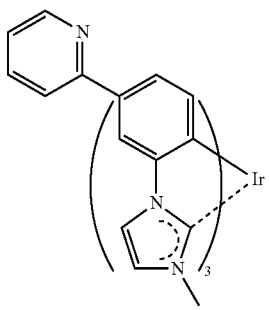
1-34
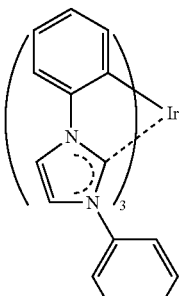
1-35
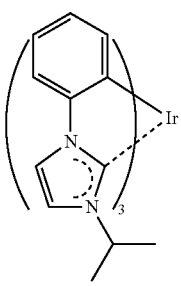
1-36
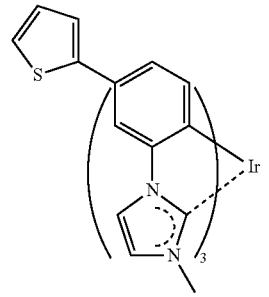

1-37
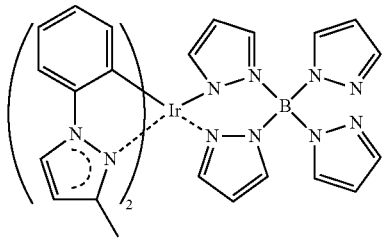
1-38
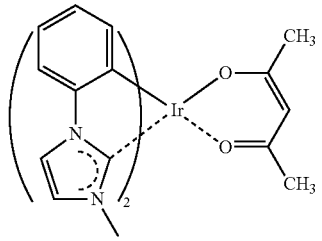
1-39
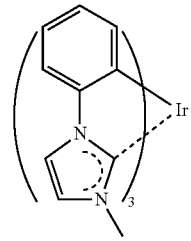
1-40
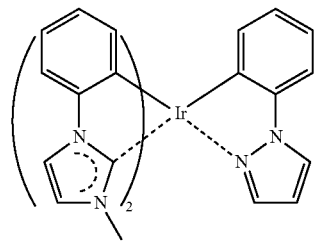
1-41
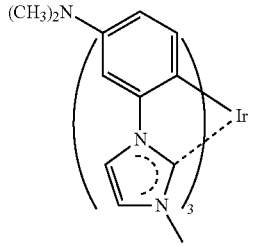
1-42
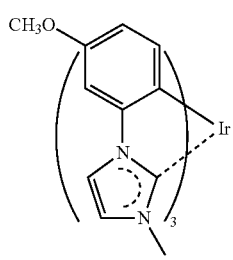
1-43
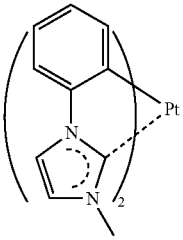
1-44
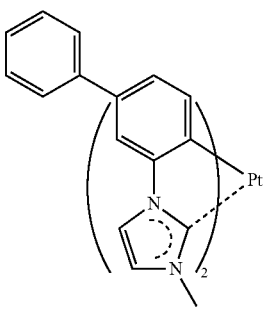
1-45
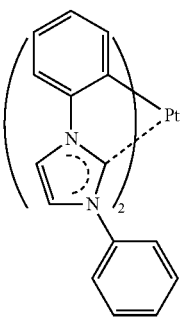
1-46
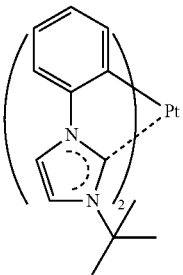
1-47
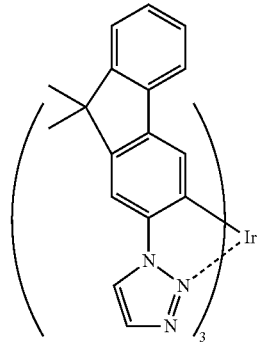

1-48
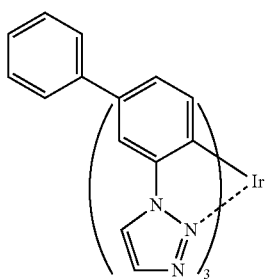
1-49
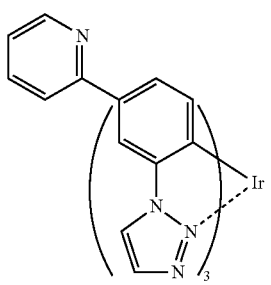
1-50
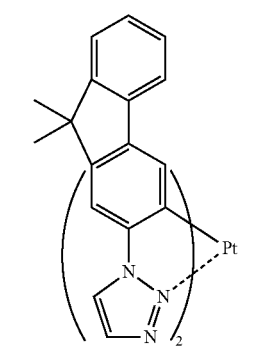
1-51
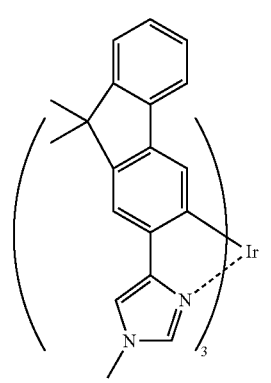
1-52
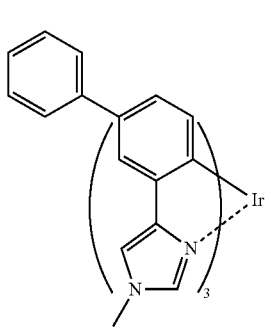
1-53
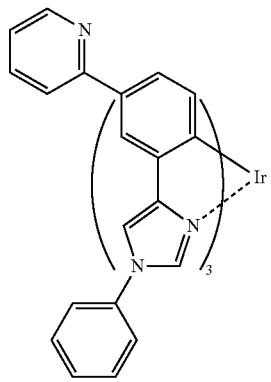
1-54
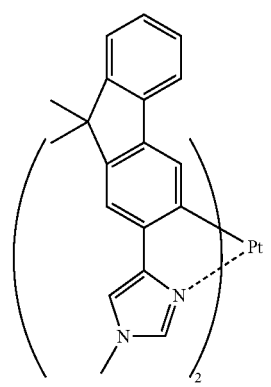
1-55
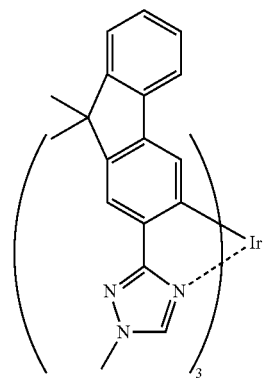
1-56
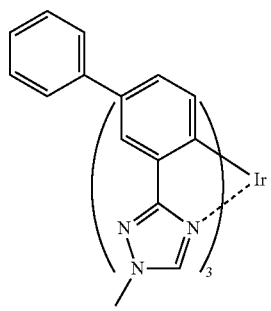

1-57
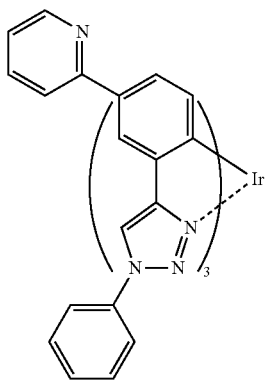
1-58
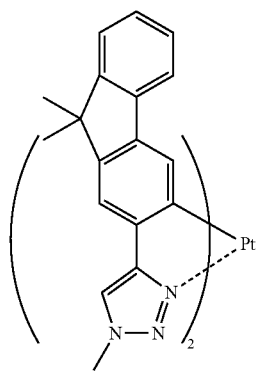
1-59
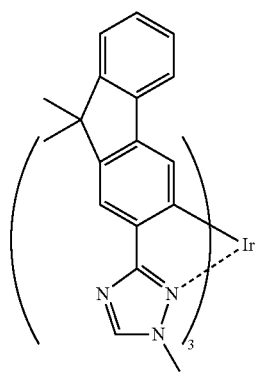
1-60
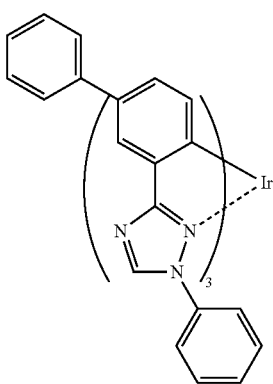
1-61
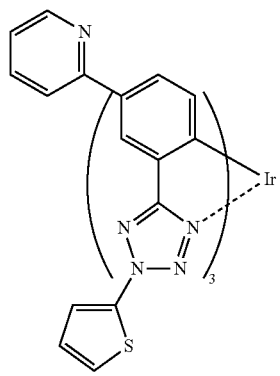
1-62
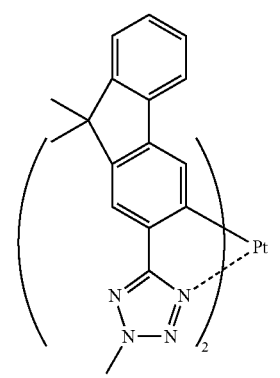
1-63
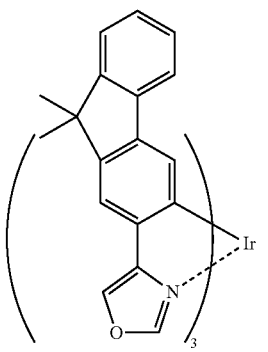
1-64
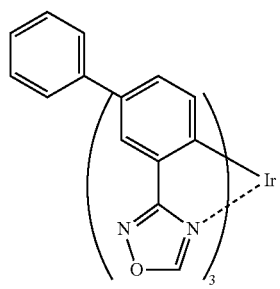

1-65
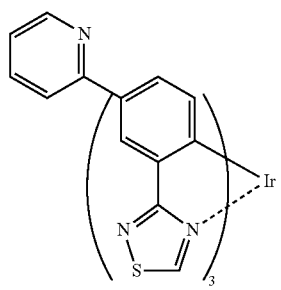
1-66
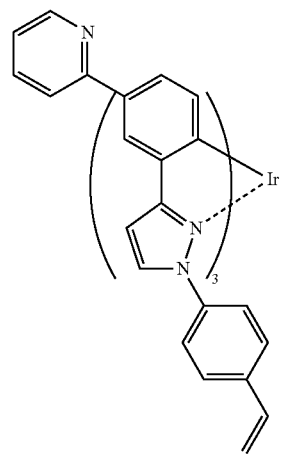
1-67
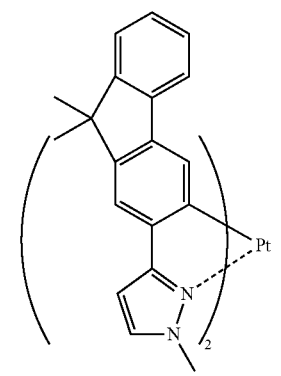
1-68
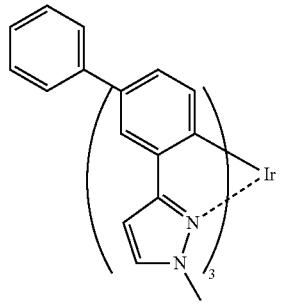
1-69
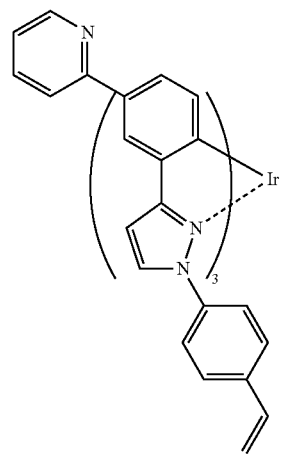
1-70
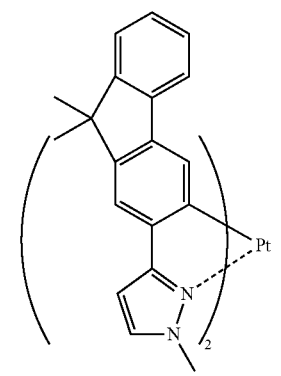
1-71
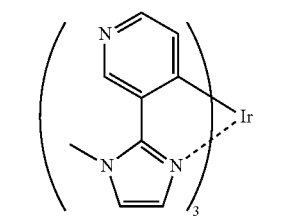
1-72
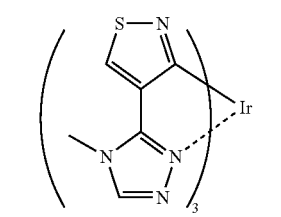
1-73
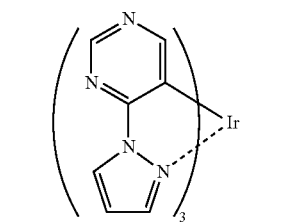

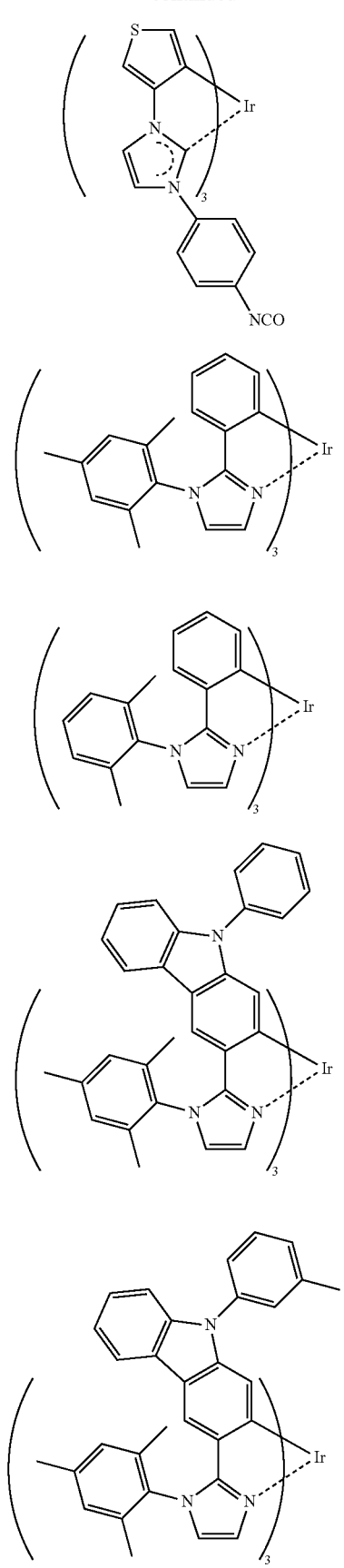
The phosphorescence emitting metal complex represented by Formula (B) of the present invention can be synthesized by referring to a method described, for example, in Inorg. Chem., Vol. 40, pages 1704-1711.

Further, in the present invention, phosphorescence emitting dopants are appropriately selected from conventional ones employed in the light emitting layer of the organic EL element and simultaneously employed Of conventional ones, as phosphorescence emitting dopants, preferred are complex based compounds incorporating metals in Groups 8-10 in the element periodic table. Of these, more preferred are iridium compounds, osmium compounds, or platinum compounds (being platinum complex based compounds), and rare earth metal complexes, and of these, most preferred are iridium compounds.

Specific examples of compounds which are employed as conventional phosphorescence emitting dopants, which may simultaneously be employed, are listed below, however the present invention is not limited thereto.

Ir-1
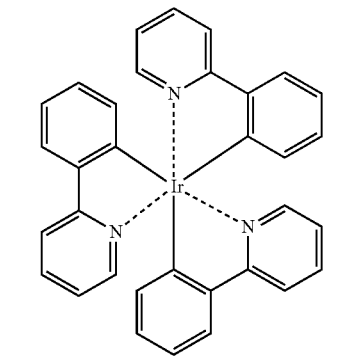

Ir-2
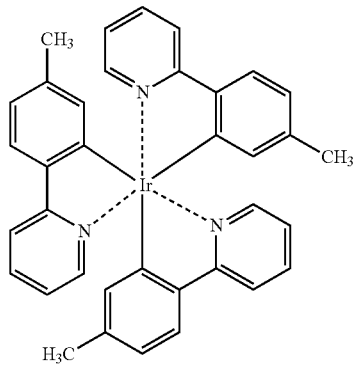

Ir-3
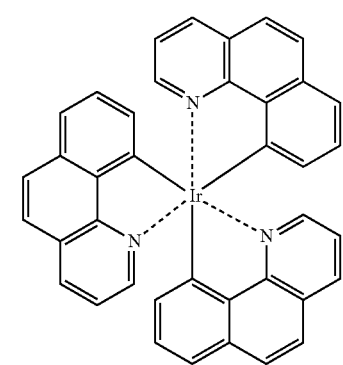

Ir-4
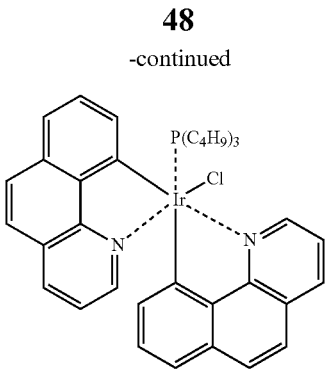

Ir-5
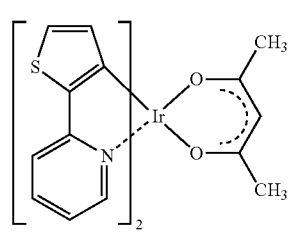

Ir-6
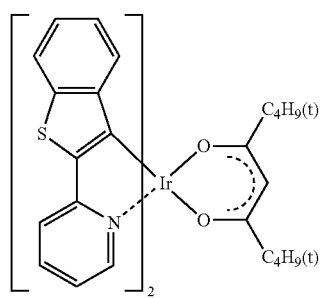

Ir-7
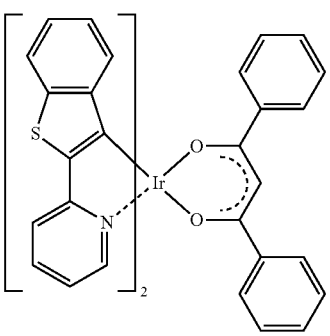

Ir-8
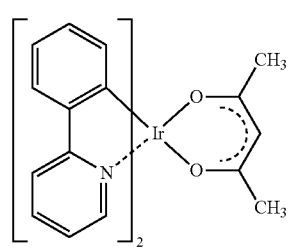

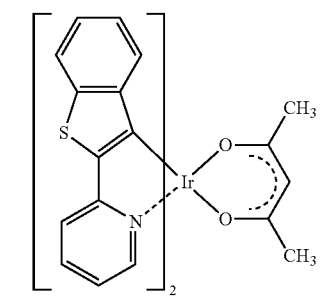
Ir-9
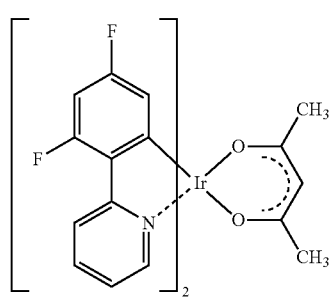
Ir-10
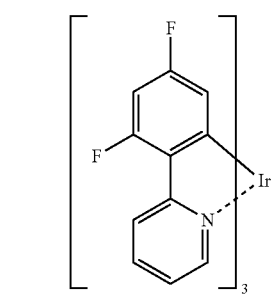
Ir-11
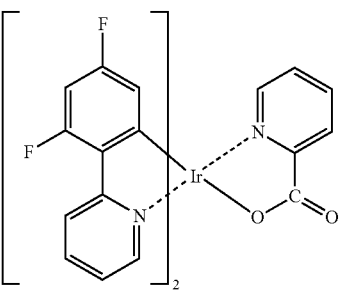
Ir-12
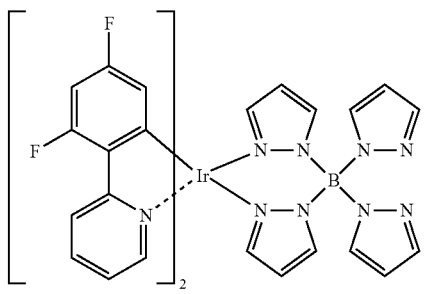
Ir-13
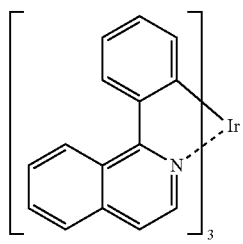
Ir-14
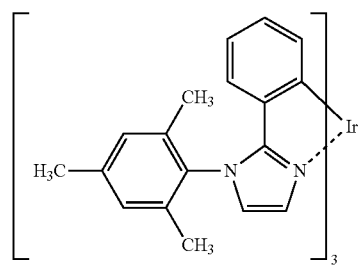
Ir-15
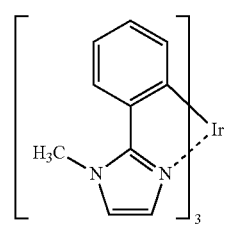
Ir-16
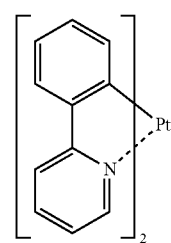
Pt-1
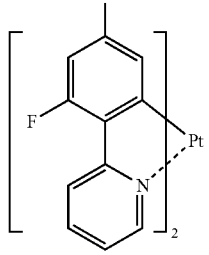
Pt-2
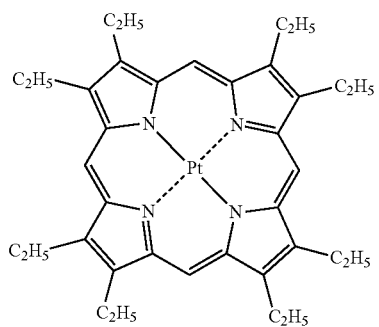
Pt-3

A-1

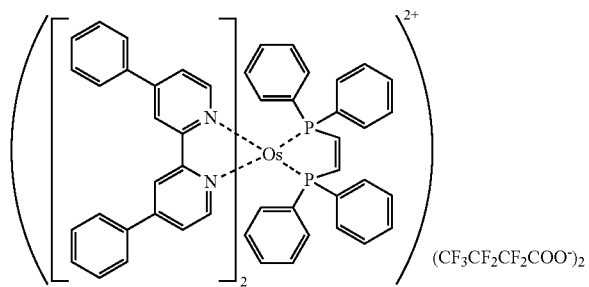

D-1

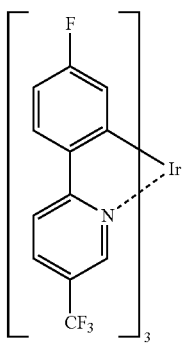

D-2

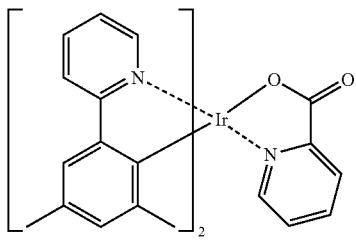

D-3

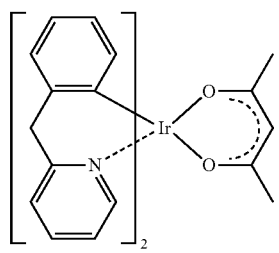

D-4

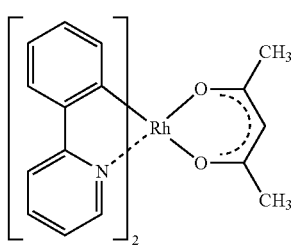

D-5

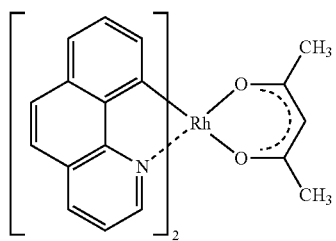

D-6

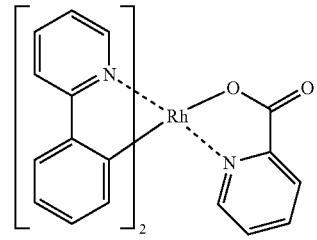

(Fluorescent Dopants (Also Referred to as Fluorescent Compounds))

As fluorescent dopants, listed are coumarin based dyes, pyran based dyes, cyanine based dyes, croconium based dyes, squarylium based dyes, oxobenzanthracene based dyes, fluorescein based dyes, Rhodamine based dyes, pyrylium based dyes, perylene based dyes, stilbene based dyes, polythiophene based dyes, or rare earth complex based fluorescent materials.

An injection layer, an inhibition layer, and an electron transport layer, which are employed as a constituting layer of the organic EL element of the present invention will now be described.

<Injection Layer: Electron Injection Layer, Positive Hole Injection Layer>

An injection layer is appropriately provided and includes an electron injection layer and a positive hole injection layer, which may be arranged between an anode and an emitting layer or a positive transfer layer, and between a cathode and an emitting layer or an electron transport layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30, 1998, published by N. T. S Corp.)", and includes a positive hole injection layer (an anode buffer layer) and an electron injection layer (a cathode buffer layer).

An anode buffer layer (a positive hole injection layer) is also detailed in such as JP-A 9-45479, 9-260062 and 8-288069, and specific examples include such as a phthalocyanine buffer layer comprising such as copper phthalocyanine, an oxide buffer layer comprising such as vanadium oxide, an amorphous carbon buffer layer, and a polymer buffer layer employing conductive polymer such as polythiophene.

A cathode buffer layer (an electron injection layer) is also detailed in such as JP-A 6-325871, 9-17574 and 10-74586, and specific examples include a metal buffer layer comprising such as strontium and aluminum, an alkali metal compound buffer layer comprising such as lithium fluoride, an alkali earth metal compound buffer layer comprising such as magnesium fluoride, and an oxide buffer layer comprising such as aluminum oxide. The above-described buffer layer (injection layer) is preferably a very thin layer, and the layer thickness is preferably in a range of 0.1-5 □m although it depends on a raw material.

<Inhibition Layer: Positive Hole Inhibition Layer, Electron Inhibition Layer>

An inhibition layer is appropriately provided in addition to the basic constitution layers composed of organic thin layers as described above. Examples are described in such as JP-A Nos. 11-204258 and 11-204359 and p. 237 of "Organic EL Elements and Industrialization Front Thereof (Nov. 30, 1998), published by N. T. S Corp.)" is applicable to a positive hole inhibition (hole block) layer according to the present invention.

A positive hole inhibition layer, in a broad meaning, is provided with a function of electron transport layer, being comprised of a material having a function of transporting an electron but a very small ability of transporting a positive hole, and can improve the recombination probability of an electron and a positive hole by inhibiting a positive hole while transporting an electron.

Further, a constitution of an electron transport layer described later can be appropriately utilized as a positive hole inhibition layer according to the present invention.

The positive hole inhibition layer of the organic EL element of the present invention is preferably arranged adjacent to the light emitting layer.

It is preferable that the positive hole inhibition layer incorporates carbazole derivatives listed as a host compound described above.

Further, in the present intention, in the case in which a plurality of light emitting layers which differ in a plurality of different emitted light colors, it is preferable that the light emitting layer which results in the shortest wavelength of the emitted light maximum wavelength is nearest to the anode in all light emitting layers. However, in such a case, it is preferable to additionally arrange the positive hole inhibition layer between the aforesaid shortest wavelength layer and the light emitting layer secondly near the anode. Further, at least 50% by weight of the compounds incorporated in the positive hole inhibition layer arranged in the aforesaid position preferably exhibits the ionization potential which is greater by at least 0.3 eV than that of the host compounds of the aforesaid shortest wavelength light emitting layer.

The ionization potential is defined as energy which is necessary to release electrons in the HOMO (being the highest occupied molecular orbital) to the vacuum level, and may be determined via, for example, the method described below.

(1) By employing Gaussian98 (Gauaaian98, Revision A. 11. 4, M. J. Frisch, et al. Gaussian 98(Gaussian98, Revision A. 11. 4, M. J. Frisch, et al, Gaussian, Inc., Pittsburgh h PA, 2002), which is a molecular orbital calculation software, produced by Gaussian Co. in the United State of America, and by employing B3LYP/6-31G* as a key word, the value (in terms of corresponding eV unit) was computed, and it is possible to obtain the ionization potential by rouging off the second decimal point. The background, in which the resulting calculated values are effective, is that the calculated values obtained by the above method exhibit high relationship with the experimental values.

(2) It is possible to determine the ionization potential via a method in which ionization potential is directly determined employing a photoelectron spectrometry. For example, by employing a low energy electron spectrophotometer "Model AC-1", produced by Riken Keiki Co., or appropriately employ a method known as an ultraviolet light electron spectrometry.

On the other hand, the electron inhibition layer, as described herein, has a function of the positive hole transport layer in a broad sense, and is composed of materials having markedly small capability of electron transport, while having capability of transporting positive holes and enables to enhance the recombination probability of electrons and positive holes by inhibiting electrons, while transporting electrons. Further, it is possible to employ the constitution of the positive hole transport layer, described below, as an electron inhibition layer when needed. The thickness of the positive hole inhibition layer and the electron transport layer according to the present invention is preferably 3-100 nm, but is more preferably 5-30 nm.

<Positive Hole Transport Layer>

A positive hole transport layer contains a material having a function of transporting a positive hole, and in a broad meaning, a positive hole injection layer and an electron inhibition layer are also included in a positive hole transport layer. A single layer of or plural layers of a positive hole transport layer may be provided.

A positive hole transport material is those having any one of a property to inject or transport a positive hole or a barrier property to an electron, and may be either an organic substance or an inorganic substance. For example, listed are a triazole derivative, an oxadiazole derivative, an imidazole derivative, a polyarylalkane derivative, a pyrazolone derivative, a phenylenediamine derivative, an arylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a positive hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include N,N,N',N'-tetraphenyl-4, 4'-diaminophenyl; N,N'-diphenyl-N,N'-bis(3-methylphenyl)-(1,1'-biphenyl)-4, 4'-diamine (TDP); 2, 2-bis(4-di-p-tolylaminophenyl)propane; 1, 1-bis(4-di-p-tolylaminophenyl)cyclohexane; N,N,N',N'-tetra-p-tolyl 4, 4'-diaminobiphenyl; 1, 1-bis(4-di-p-tolylaminophenyl)-4-phenylcyclohexane; bis(4-dimethylamino-2-methyl)phenylmethane; bis(4-di-p-tolylaminophenyl)phenylmethane; N,N'-diphenyl-N,N'-di(4-methoxyphenyl)-4, 4'-diaminobiphenyl; N,N,N',N'-tetraphenyl-4, 4'-diaminophenylether; 4, 4'-bis(diphenylamino)quadriphenyl; N,N,N-tri(p-tolyl) amine; 4-(di-p-tolylamino)-4'-[4-(di-p-triamino)styryl]stilbene; 4-N,N-diphenylamino-(2-diphenylvinyl)benzene; 3-methoxy-4'-N,N-diphenylaminostilbene; and N-phenylcarbazole, in addition to those having two condensed aromatic rings in a molecule described in U.S. Pat. No. 5,061, 569, such as 4, 4'-bis[N-(1-naphthyl)-N-phenylamino] biphenyl (NDP), and 4,4',4"-tris[N-(3-methylphenyl)-N-phenylamino]triphenylamine (MDTDATA), in which three of triphenylamine units are bonded in a star burst form, described in JP-A 4-308688.

Polymer materials, in which these materials are introduced in a polymer chain or constitute the main chain of polymer, can be also utilized. Further, an inorganic compound such as a p type-Si and a p type-SiC can be utilized as a positive hole injection material and a positive hole transport material Further, it is possible to employ so-called p type positive hole transport materials, as described in Japanese Patent Publication Open to Public Inspection (hereinafter referred to as JP-A) No. 11-251067, and J. Huang et al. reference (Applied Physics Letters 80(2002), p. 139). In the present invention, since high efficiency light emitting elements are prepared, it is preferable to employ these materials.

This positive hole transport layer can be prepared by forming a thin layer made of the above-described positive hole transport material according to a method well known in the art such as a vacuum evaporation method, a spin coating method, a cast method, an inkjet method and a LB method.

The layer thickness of a positive hole transport layer is not specifically limited, however, it is generally 5 nm-5 nm, and preferably 5 nm-200 nm. This positive transport layer may have a single layer structure comprised of one or not less than two types of the above described materials.

Further, it is possible to employ a positive hole transport layer of a higher p property which is doped with impurities. As its example, listed are those described in each of JP-A Nos. 4-297076, 2000-196140, 2001-102175, as well as in J. Appl. Phys., 95,5773 (2004).

In the present invention, it is preferable to employ a positive hole transport layer of such a high p property, since it is possible to produce an element of lower electric power consumption.

<Electron Transport Layer>

An electron transport layer is comprised of a material having a function to transfer an electron, and an electron injection layer and a positive hole inhibition layer are included in an electron transport layer in a broad meaning. A single layer or plural layers of an electron transport layer may be provided.

Heretofore, when an electron transport layer is composed of single layer and a plurality of layers, electron transport materials (also functioning as a positive hole inhibition material) employed in the electron transport layer adjacent to the cathode side with respect to the light emitting layer, electrons ejected from the cathode may be transported to the light emitting layer. As such materials, any of the conventional compounds may be selected and employed.

Examples of these compounds include such as a nitro-substituted fluorene derivative, a diphenylquinone derivative, a thiopyradineoxide derivative, carbodiimide, a fluorenylidenemethane derivative, anthraquinonedimethane, an anthraquinone derivative, an anthrone derivative and an oxadiazole derivative.

Further, a thiazole derivative in which an oxygen atom in the oxadiazole ring of the above-described oxadiazole derivative is substituted by a sulfur atom, and a quinoxaline derivative having a quinoxaline ring which is known as an electron attracting group can be utilized as an electron transport material.

Polymer materials, in which these materials are introduced in a polymer chain or these materials form the main chain of polymer, can be also utilized.

Further, a metal complex of a 8-quinolinol derivative such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transport material.

Further, metal-free or metal phthalocyanine, or those the terminal of which is substituted by an alkyl group and a sulfonic acid group, can be preferably utilized as an electron transport material. Further, distyrylpyrazine derivative, which has been exemplified as a material of an emitting layer, can be also utilized as an electron transport material, and, similarly to the case of a positive hole injection layer and a positive hole transfer layer, an inorganic semiconductor such as an n-type-Si and an n-type-SiC can be also utilized as an electron transport material.

This electron transport layer can be prepared by forming a thin layer made of the above-described electron transport material according to a method well known in the art such as a vacuum evaporation method, a spin coating method, a cast method, an inkjet method and a LB method.

The layer thickness of an electron transport layer is not specifically limited; however, it is generally 5 nm-5 nm, and preferably 5 nm-200 nm. This electron transport layer may have a single layer structure comprised of one or not less than two types of the above described materials.

Further, it is possible to employ an electron transport layer doped with impurities, which exhibits high n property. Examples thereof include those, described in JP-A Nos. 4-297076, 10-270172, 2000-196140, 2001-102175, as well as J. Appl. Phys., 95, 5773 (2004).

The present invention is preferable since by employing an electron transport layer of such a high n property electron transport layer, it is possible to preparer an element of further lowered electric power consumption.<Anode>

As an anode according to an organic EL element of the present invention, those comprising metal, alloy, a conductive compound, which is provided with a large work function (not less than 4 eV), and a mixture thereof as an electrode substance are preferably utilized. Specific examples of such an electrode substance include a conductive transparent material such as metal like Au, CuI, indium tin oxide (ITO), SnO2 and ZnO. Further, a material such as IDIXO (In2O3-ZnO), which can prepare an amorphous and transparent electrode, may be also utilized.

As for an anode, these electrode substances may be made into a thin layer by a method such as evaporation or spattering and a pattern of a desired form may be formed by means of photolithography, or in the case of requirement of pattern precision is not so severe (not less than 100 nm), a pattern may be formed through a mask of a desired form at the time of evaporation or spattering of the above-described substance.

Alternatively, when coatable materials such as organic electrically conductive compounds are employed, it is possible to employ a wet system filming method such as a printing system or a coating system.

When emission is taken out of this anode, the transmittance is preferably set to not less than 10% and the sheet resistance as an anode is preferably not more than a few hundreds $\Omega/\square$. Further, although the layer thickness depends on a material, it is generally selected in a range of 10-1,000 nm and preferably of 10-200 nm.

<Cathode>

On the other hand, as a cathode according to the present invention, metal, alloy, a conductive compound and a mixture thereof, which have a small work function (not more than 4 eV), are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are a mixture of electron injecting metal with the second metal which is stable metal having a work function larger than electron injecting metal, such as a magnesium/silver mixture, a magnesium/aluminum mixture, a magnesium/indium mixture, an aluminum/aluminum oxide ($Al_2O_3$) mixture and a lithium/aluminum mixture, and aluminum. As for a cathode, these electrode substances may be made into a thin layer by a method such as evaporation or spattering.

Further, the sheet resistance as a cathode is preferably not more than a few hundreds Ω/□ and the layer thickness is generally selected in a range of 10 nm-5 nm and preferably of 50-200 nm.

Herein, to transmit emission, either one of an anode or a cathode of an organic EL element is preferably transparent or translucent to improve the mission luminance Further, after forming, on the cathode, the above metals at a film thickness of 1-20 nm, it is possible to prepare a transparent or translucent cathode in such a manner that electrically conductive transparent materials are prepared thereon. By applying the above, it is possible to produce an element in which both anode and cathode are transparent.

<Substrate>

A substrate according to an organic EL element of the present invention is not specifically limited with respect to types of such as glass and plastics. They me be transparent or opaque.

However, a transparent substrate is preferable when the emitting light is taken from the side of substrate. Substrates preferably utilized includes such as glass, quartz and transparent resin film. A specifically preferable substrate is resin film capable of providing an organic EL element with a flexible property.

Resin film includes such as: polyesters such as polyethylene terephthalate (PET) and polyethylene naphthalate (PEN); polyethylene, polypropyrene; cellulose esters or their derivatives such as cellophane, cellulose diacetate, cellulose triacetate, cellulose acetate butylate, cellulose acetate propionate (CAP), cellulose acetate phthalate (TAC) and cellulose nitrate; polyvinylidene chloride, polyvinyl alcohol, polyethylene vinyl alcohol, syndiotactic polystyrene, polycarbonate, norbornene resin, polymethylpentene, polyether ketone, polyimide, polyether sulfone (PES), polyphenylene sulfide, polysulfones, polyetherimide, polyether ketone imide, polyamide, fluororesin, Nylon, polymethylmethacrylate, acrylic resin, polyacrylate; and cycloolefine resins such as ARTON (produced by JSR Co. Ltd.) and APEL (produce by Mitsui Chemicals, Inc.)

On the surface of a resin film, formed may be a film incorporating inorganic and organic compounds or a hybrid film of both. Barrier films are preferred at a water vapor permeability (25±0.5° C., and relative humidity (90±2)% RH) of at most 0.01 g/(m$^2$·24 h), determined based on JIS K 7129-1992. Further, high barrier films are preferred at an oxygen permeability of at most $1\times10^{-3}$ ml/(m$^2$·24 h·MPa), and at a water vapor permeability of at most $10^{-5}$ g/(m$^2$·24 h), determined based on JIS K 7126-1987.

As materials forming a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited, and examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel, films, opaque resin substrates, and ceramic substrates.

The external extraction efficiency of light emitted by the organic EL element of the present invention is preferably at least 1% at room temperature, but is more preferably at least 5%.

External extraction quantum yield (%)=the number of photons emitted by the organic EL element to the exterior/ the number of electrons fed to organic EL element Further, even by simultaneously employing color hue improving filters such as a color filter, simultaneously employed may be color conversion filters which convert emitted light color from the organic EL element to multicolor by employing fluorescent materials. When the color conversion filters are employed, it is preferable that λmax of light emitted by the organic EL element is at least 480 nm.

<<Sealing>>

As sealing means employed in the present invention, listed may be, for example, a method in which sealing members, electrodes, and a supporting substrate are subjected to adhesion via adhesives.

The sealing members may be arranged to cover the display region of an organic EL element, and may be an engraved plate or a flat plate. Neither transparency nor electrical insulation is limited.

Specifically listed are glass plates, polymer plate-films, metal plates, and films. Specifically, it is possible to list, as glass plates, soda-lime glass, barium-strontium containing glass, lead glass, aluminosilicate glass, borosilicate glass, bariumborosilicate glass, and quartz.

Further, listed as polymer plates may be polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to convert the element to a thin film, it is possible to preferably employ a metal film. Further, the oxygen permeability of the polymer film is preferably at most $1\times10^{-3}$ ml/(m$^2$·24 h·MPa), determined by the method based on JIS K 7126-1987, while its water vapor permeability (at 25±0.5° C. and relative humidity (90±2)%) is at most $10^{-5}$ g/(m$^2$·24 h), determined by the method based on JIS K 7129-1992.

Conversion of the sealing member into concave is carried out employing a sand blast process or a chemical etching process. In practice, as adhesives, listed may be photo-curing and heat-curing types having a reactive vinyl group of acrylic acid based oligomers and methacrylic acid, as well as moisture curing types such as 2-cyanoacrylates.

Further listed may be thermal and chemical curing types (mixtures of two liquids) such as epoxy based ones. Still further listed may be hot-melt type polyamides, polyesters, and polyolefins. Yet further listed may be cationically curable type ultraviolet radiation curable type epoxy resin adhesives.

In addition, since an organic EL element is occasionally deteriorated via a thermal process, those are preferred which enable adhesion and curing between room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials forming the aforesaid film may be those which exhibit functions to retard penetration of those such as moisture or oxygen which results in deterioration. For example, it is possible to employ silicon oxide, silicon dioxide, and silicon nitride.

Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

In a gas phase and a liquid phase, it is preferable to inject inert gases such as nitrogen or argon, and inactive liquids such as fluorinated hydrocarbon or silicone oil into the space between the sealing member and the surface region of the organic EL element. Further, it is possible to form vacuum. Still further, it is possible to enclose hygroscopic compounds in the interior.

Examples of hygroscopic compounds include metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides.

<<Protective Film and Protective Plate>>

The aforesaid sealing film on the side which nips the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, whereby it is preferable to arrange the protective film or the protective plate described above. Usable materials for these include glass plates, polymer plate-films, and metal plate-films which are similar to those employed for the aforesaid sealing. However, in terms of light weight and a decrease in thickness, it is preferable to employ polymer films.

<<Light Extraction>>

It is generally known that an organic EL element emits light in the interior of the layer exhibiting the refractive index (being about 1.7-about 2.1) which is greater than that of air, whereby only about 15-about 20% of light generated in the light emitting layer is extracted.

This is due to the fact that light incident to an interface (being an interface of a transparent substrate to air) at an angle of θ which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction of the element side surface.

Means to enhance the efficiency of the aforesaid light extraction include, for example, a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between the substrate and any of the layers such as the transparent electrode layer or the light emitting layer (including between the substrate and the outside).

By combining these means, the present invention enables the production of elements which exhibit higher luminance or excel in durability.

When a low refractive index medium of a thickness, which is greater than the wavelength of light, is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5-about 1.7, the refractive index of the low refractive index layer is preferably at most approximately 1.5, but is more preferably at most 1.35.

Further, thickness of the low refractive index medium is preferably at least two times the wavelength in the medium. The reason is that when the thickness of the low refractive index medium reaches nearly the wavelength of light so that electromagnetic waves oozed via evernescent enter into the substrate, effects of the low refractive index layer are lowered.

The method in which the interface which results in total reflection or a diffraction grating is introduced in any of the media is characterized in that light extraction efficiency is significantly enhanced.

The above method works as follows. By utilizing properties of the diffraction grating capable of changing the light direction to the specific direction different from diffraction via so-called Bragg diffraction such as primary diffraction or secondary diffraction of the diffraction grating, of light emitted from the light emitting layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced.

However, by changing the refractive index distribution to a two-dimensional one, light, which travels to all directions, is diffracted, whereby the light extraction efficiency is enhanced.

As noted above, a position to introduce a diffraction grating may be between any layers or in a medium (in a transparent substrate or a transparent electrode). However, a position near the organic light emitting layer, where light is generated, is desirous.

In this case, the cycle of the diffraction grating is preferably about 1/2-about 3 times the wavelength of light in the medium.

The preferable arrangement of the diffraction grating is such that the arrangement is two-dimensionally repeated in the form of a square lattice, a triangular lattice, or a honeycomb lattice.

<<Light Collection Sheet>>

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 µm and an apex angle of 90 degrees are two-dimensionally arranged on the light extraction side of the substrate. The side length is preferably 10-100 µm. When it is less than the lower limit, coloration results due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited. As shapes of a prism sheet employed may be, for example, shaped stripes of an apex angle of 90 degrees and a pitch of 50 µm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

<<Preparation Method of Organic EL Element>>

As one example of the preparation method of the organic EL element of the present invention, the preparation method of the organic EL element composed of anode/positive hole injection layer/positive hole transport layer/light emitting layer/electron transport layer/electron injection layer/cathode will be described.

Initially, a thin film composed of desired electrode substances, for example, anode substances is formed on an appropriate base material to reach a thickness of at most 1 µm but preferably 10-200 nm, employing a method such as vapor deposition or sputtering, whereby an anode is prepared.

Subsequently, on the above, formed are organic compound thin layers including a positive hole injection layer, a positive hole transport layer, a light emitting layer, a positive hole inhibition layer, an electron transport layer, and an electron injection layer, which are organic EL element materials.

Methods to form each of these layers include, as described above, a vapor deposition method and a wet process (a spin coating method, a casting method, an ink-jet method, and a printing method). In the present invention, in view of easy formation of a homogeneous film and rare formation of pin holes, preferred is film formation via the coating method such as the spin coating method, the ink-jet method, or the printing method, and of these, the ink-jet method is particularly preferred.

In the present invention, during formation of the light emitting layer, it is preferable that the layer is formed via a coating method employing a liquid which is prepared by dissolving or dispersing organic metal complexes according to the present invention. It is specifically preferable that the coating method is the ink-jet method.

As liquid media which are employed to dissolve or disperse organic metal complexes according to the present invention, employed may be, for example, ketones such as methyl ethyl ketone or cyclohexanone, fatty acid esters such as ethyl acetate, halogenated hydrocarbons such as dichlorobenzene, and organic solvents such as DMF or DMSO.

Further, with regard to dispersion methods, it is possible to achieve dispersion employing dispersion methods such as ultrasonic waves, high shearing force dispersion or media dispersion.

After forming these layers, a thin layer composed of cathode materials is formed on the above layers via a method such as vapor deposition or sputtering so that the film thickness reaches at most 1 µm, but is preferably in the range of 50-200 nm, whereby a cathode is arranged, and the desired organic EL element is prepared.

Further, by reversing the preparation order, it is possible to achieve preparation in order of a cathode, an electron injection layer, an electron transport layer, a light emitting layer, a positive hole transport layer, a positive hole injection layer, and an anode. When direct current voltage is applied to the multicolor display device prepared as above, the anode is employed as + polarity, while the cathode is employed as −polarity. When 2-40 V is applied, it is possible to observe light emission. Further, alternating current voltage may be applied. The wave form of applied alternating current voltage is not specified.

<<Application>>

It is possible to employ the organic EL element of the present invention as display devices, displays, and various types of light emitting sources. Examples of light emitting sources include, but are not limited to lighting apparatuses (home lighting and car lighting), clocks, backlights for liquid crystals, sign advertisements, signals, light sources of light memory media, light sources of electrophotographic copiers, light sources of light communication processors, and light sources of light sensors.

It is effectively employed especially as backlights of liquid crystal display devices and lighting sources.

If needed, the organic EL element of the present invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

Figure 4:
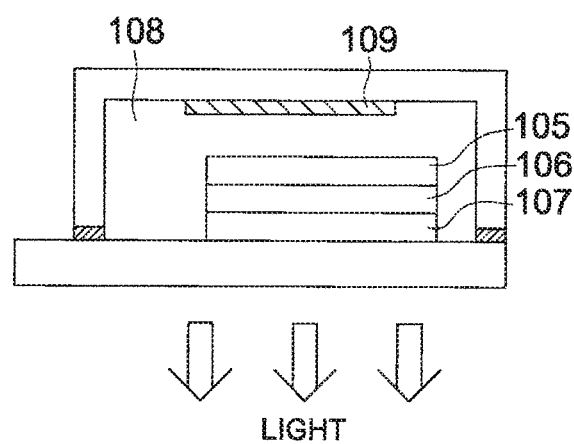
FIG. 4 is a schematic cross-sectional view of a lighting device.

Color of light emitted by the organic EL element of the present invention and compounds according to the present invention is specified as follows. In FIG. 4.16 on page 108 of "Shinpen Shikisai Kagaku Handbook (New Edition Color Science Handbook)" (edited by The Color Science Association of Japan, Tokyo Daigaku Shuppan Kai, 1985), values determined via a spectroradiometric luminance meter CS-1000 (produced by Konica Minolta Sensing Inc.) are applied to the CIE chromaticity coordinate, whereby the color is specified.

Further, when the organic EL element of the present invention is a white element, "white", as described herein, means that when 2-degree viewing angle front luminance is determined via the aforesaid method, chromaticity in the CIE 1931 Color Specification System is within the region of $X=0.33\pm0.07$ and $Y=0.33\pm0.07$.

EXAMPLES

The present invention will now be described with reference to examples, however the present invention is not limited thereto.

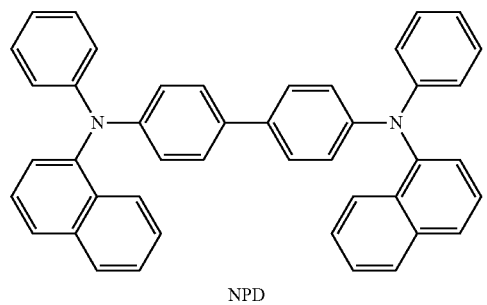

NPD

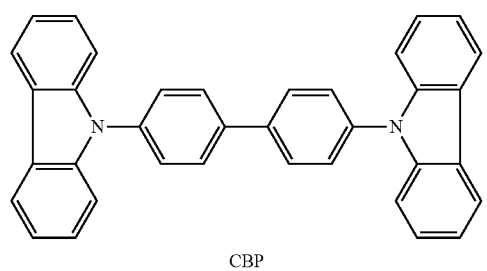

CBP

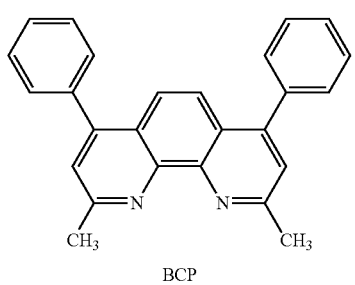

BCP

-continued

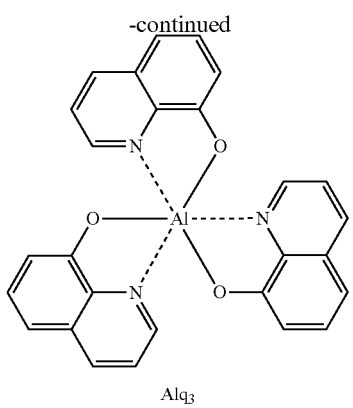

Alq$_3$

Example 1

<<Preparation of Organic EL Element 1-1>>

Patterning was applied to a substrate (NA45 produced by NH Techno Glass Corp.) on which a 100 nm film of ITO (indium tin oxide) was formed, as a anode, on the above 100 mm×100 mm×1.1 mm glass substrate. Thereafter, the above transparent support substrate provided with the ITO transparent electrode underwent ultrasonic washing with isopropyl alcohol, dried via desiccated nitrogen gas, and underwent UV ozone washing for 5 minutes.

The resulting transparent support substrate was fixed via the substrate holder of a commercial vacuum deposition apparatus. Separately, 200 mg of α-NPD was placed in a molybdenum resistance heating boat, 200 mg of CBP as a host compound was placed in another molybdenum resistance heating boat, 200 mg of BCP was placed in further another molybdenum resistance heating boat, 100 mg of Exemplified Compound 1-1 was placed in yet another molybdenum resistance heating boat, and 200 mg of Alq3 was placed in still yet another molybdenum resistance heating boat, and the resulting boats were fitted in the vacuum deposition apparatus.

Subsequently, after reducing the pressure of the vacuum tank to $4\times10^{-4}$ Pa, the aforesaid heating boat, in which α-NPD was placed, was heated via application of electric current and deposition was carried out onto the transparent support substrate at a deposition rate of 0.1 nm/second, whereby a 40 nm thick positive hole transport layer was arranged.

Further, the aforesaid heating boats in which CBP and Exemplified Compound 1-1 were placed respectively, were heated via application of electric current and co-deposition was carried out onto the aforesaid positive hole transport layer at a deposition rate of 0.2 nm/second and 0.012 nm/second, respectively, whereby a 40 nm thick light emitting layer was arranged. The substrate during deposition had a room temperature.

Further, the aforesaid heating boat, in which BCP was placed, was heated via application of electric current and deposition was carried out onto the aforesaid light emitting layer at a deposition rate of 0.1 nm/second, whereby a 10 nm thick positive hole inhibition layer was arranged.

Further, the aforesaid heating boat, in which Alq3 was placed, was heated via application of electric current and deposition was carried out onto the aforesaid positive hole inhibition layer at a deposition rate of 0.1 nm/second, whereby a 40 nm thick electron transport layer was arranged. The substrate during deposition had a room temperature.

Subsequently, 0.5 nm lithium fluoride and 110 nm aluminum were deposited to form a cathode, whereby Organic EL Element 1-1 was prepared.

<<Preparation of Organic EL Elements 1-2 through 1-15>>

Organic EL Elements 1-2 through 1-15 were prepared in the same manner as Organic EL Element 1-1, except that CBP which was the host compound in the light emitting layer was replaced with each of the compounds listed in Table 1, and Exemplified Compound 1-1 was replaced with each of the compounds listed in Table 1.

<<Evaluation of Organic EL Elements 1-1 through 1-15>>

Prepared Organic EL Elements 1-1 through 1-15 were evaluated. Table 1 shows the results.

<<Evaluation of Organic EL Elements>>

The prepared Organic EL Elements 1-1 through 1-16 were evaluated as follows. The non-light emitting surface of each of the organic EL elements was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the illuminating device shown in FIGS. 3 and 4 was formed, followed by evaluation.

Figure 3:
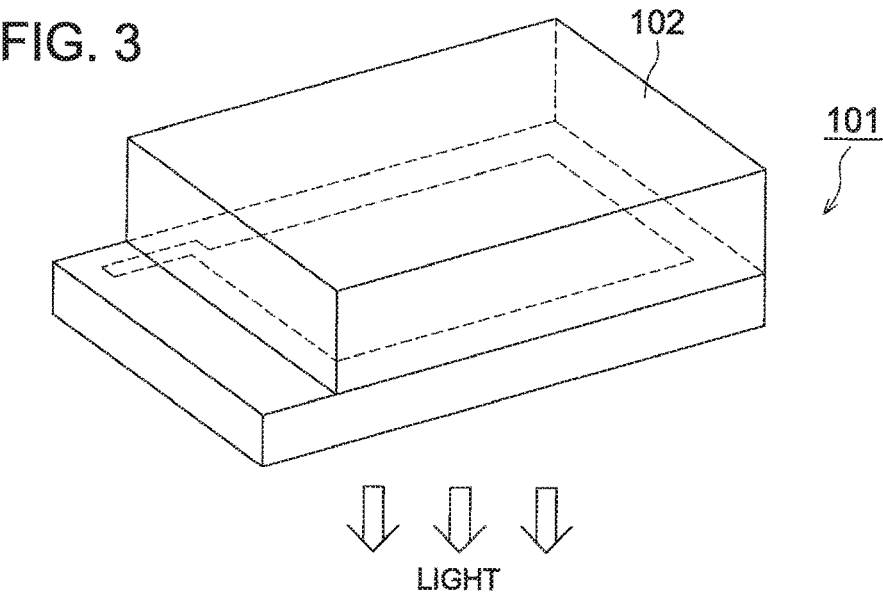
FIG. 3 is a schematic drawing of a lighting device.

FIG. 3 is a schematic view of the illuminating device and Organic EL Element 101 is covered with glass cover 102 (incidentally, sealing by the glass cover was carried out in a globe box under nitrogen ambience (under an ambience of high purity nitrogen gas at a purity of at least 99.999%) so that Organic EL Element 101 was not brought into contact with atmosphere.

FIG. 4 is a cross-sectional view of an illuminating device, and in FIG. 4, 105 represents a cathode, 106 represents an organic EL layer, and 107 represents a glass substrate fitted with a transparent electrode. Further, the interior of glass cover 102 is filled with nitrogen gas 108 and water catching agent 109 is provided.

<<External Extraction Quantum Efficiency>>

Constant electric current of 2.5 mA/cm$^2$ was applied to the prepared organic EL element at 23° C. under an ambience of desiccated nitrogen gas, and the external extraction quantum efficiency (%) was determined. A spectroradiometric luminance meter CS-1000 (produced by Konica Minolta Inc.) was employed for the above determination.

The external extraction quantum efficiency in Table 1 was represented by the relative value when the external extraction quantum efficiency of Organic EL Element 1-15 was 100.

<<Lifetime>>

When driven at a constant electric current of 2.5 mA/cm$^2$, the time which was required for a decease in one half of the luminance immediately after the initiation of light emission (being the initial luminance) was determined, and the resulting value was employed as an index of the lifetime in terms of a half lifetime (τ0.5). Meanwhile, a spectroradiometric luminance meter CS-1000 (produced by Konica Minolta Inc.) was employed for the above determination. Further, the lifetime in Table 1 is represented by a relative value when the lifetime of Organic EL Element 1-1 was 100. Table 1 shows the results.

TABLE 1

| Organic EL Element No. | Dopant Compound | Host Compound | External Extraction Quantum Efficiency | Lifetime | Remarks |
| --- | --- | --- | --- | --- | --- |
| 1-1 | 1-1 | CBP | 100 | 100 | Comp. |
| 1-2 | 1-75 | CBP | 115 | 130 | Comp. |
| 1-3 | 1-77 | CBP | 90 | 120 | Comp. |
| 1-4 | 1-1 | 1 | 130 | 160 | Inv. |
| 1-5 | 1-1 | 22 | 132 | 155 | Inv. |
| 1-6 | 1-1 | 29 | 128 | 150 | Inv. |
| 1-7 | 1-1 | 38 | 126 | 153 | Inv. |
| 1-8 | 1-1 | 41 | 127 | 150 | Inv. |
| 1-9 | 1-75 | 1 | 145 | 250 | Inv. |
| 1-10 | 1-75 | 6 | 140 | 230 | Inv. |
| 1-11 | 1-75 | 17 | 142 | 228 | Inv. |
| 1-12 | 1-75 | 22 | 141 | 230 | Inv. |
| 1-13 | 1-75 | 25 | 138 | 235 | Inv. |
| 1-14 | 1-75 | 27 | 136 | 231 | Inv. |
| 1-15 | 1-75 | 28 | 136 | 238 | Inv. |
| 1-16 | 1-75 | 29 | 139 | 227 | Inv. |
| 1-17 | 1-75 | 38 | 140 | 228 | Inv. |
| 1-18 | 1-75 | 41 | 142 | 230 | Inv. |
| 1-19 | 1-77 | 1 | 128 | 210 | Inv. |
| 1-20 | 1-77 | 22 | 125 | 202 | Inv. |
| 1-21 | 1-77 | 29 | 122 | 209 | Inv. |
| 1-22 | 1-77 | 38 | 123 | 205 | Inv. |
| 1-23 | 1-77 | 41 | 129 | 200 | Inv. |

Comp.: Comparative Example,
Inv.: Present Invention

As can clearly be seen from Table 1, organic EL elements of the present invention achieved high efficiency and long lifetime, compared with comparative examples.

Example 2

<<Preparation of Organic EL Element 2-1>>

Patterning was applied to a substrate (NA45 produced by NH Techno Glass Corp.) on which a 100 nm film of ITO (indium tin oxide) was formed, as a anode, on the above 100 mm×100 mm×1.1 mm glass substrate. Thereafter, the above transparent support substrate provided with the ITO transparent electrode underwent ultrasonic washing with isopropyl alcohol, dried via desiccated nitrogen gas, and underwent UV ozone washing for 5 minutes.

The resulting transparent support substrate was fixed via the substrate holder of a commercial vacuum deposition apparatus. Separately, 200 mg of α-NPD was placed in a molybdenum resistance heating boat, 200 mg of CBP as a host compound was placed in another molybdenum resistance heating boat, 100 mg of Ir-1 was placed in further another molybdenum resistance heating boat, and 200 mg of Alq3 was placed in still further another molybdenum resistance heating boat, and the resulting boats were fitted in the vacuum deposition apparatus.

Subsequently, after reducing the pressure of the vacuum tank to 4×10$^{-4}$ Pa, the aforesaid heating boat, in which α-NPD was placed, was heated via application of electric current and deposition was carried out onto the transparent support substrate at a deposition rate of 0.1 nm/second, whereby a 40 nm thick positive hole transport layer was arranged.

Further, the aforesaid heating boats in which CBP and Ir-1 were placed respectively, were heated via application of electric current, and co-deposition was carried out onto the aforesaid positive hole transport layer at a deposition rate of 0.2 nm/second and 0.012 nm/second, respectively, whereby a 40 nm thick light emitting layer was arranged. The substrate during deposition had a room temperature.

Further, the aforesaid heating boat, in which BCP was placed, was heated via application of electric current and deposition was carried out onto the aforesaid light emitting layer at a deposition rate of 0.1 nm/second, whereby a 10 nm thick positive hole inhibition layer was arranged.

Still further, the aforesaid heating boat, in which Alq3 was placed, was heated via application of electric current, and deposition was carried out onto the aforesaid positive hole inhibition layer at a deposition rate of 0.1 nm/second, whereby a 40 nm thick electron transport layer was arranged.

Meanwhile, the substrate during deposition had a room temperature.

Subsequently, 0.5 nm lithium fluoride and 110 nm aluminum were deposited to form a cathode, whereby Organic EL Element 2-1 was prepared.

<<Preparation of Organic EL Elements 2-2 Through 2-15>>

Organic EL Elements 2-2 through 2-15 were prepared in the same manner as Organic EL Element 2-1, except that CBP which was the host compound in the light emitting layer was replaced with each of the compounds listed in Table 2, and Ir-1 employed as a dopant compound in the light emitting layer was replaced with each of the compounds listed in Table 2.

<<Evaluation of Organic EL Elements 2-1 through 2-28>>

Prepared Organic EL Elements 2-1 through 2-28 were evaluated in the same manner as Example 1. Table 2 shows the results.

Meanwhile, in Table 2, each of the external extraction quantum efficiency and the lifetime is represented by a relative value when each of the external extraction quantum efficiency and the lifetime of Organic EL Element 2-2 was 100. Table 2 shows the results.

TABLE 2

| Organic EL Element No. | Dopant Compound | Host Compound | External Extraction Quantum Efficiency | Lifetime | Remarks |
|---|---|---|---|---|---|
| 2-1 | Ir-1 | CBP | 100 | 100 | Comp. |
| 2-2 | 1-83 | CBP | 103 | 105 | Comp. |
| 2-3 | Ir-1 | 1 | 120 | 135 | Inv. |
| 2-4 | 1-83 | 1 | 127 | 150 | Inv. |
| 2-5 | Ir-1 | 22 | 113 | 124 | Inv. |
| 2-6 | Ir-1 | 29 | 116 | 120 | Inv. |
| 2-7 | Ir-1 | 38 | 118 | 119 | Inv. |
| 2-8 | Ir-1 | 41 | 119 | 123 | Inv. |
| 2-9 | 1-83 | 22 | 120 | 148 | Inv. |
| 2-10 | 1-83 | 29 | 121 | 145 | Inv. |
| 2-11 | 1-83 | 38 | 122 | 148 | Inv. |
| 2-12 | 1-83 | 41 | 118 | 144 | Inv. |

Comp.: Comparative Example,
Inv.: Present Invention

As can clearly be seen from Table 2, organic EL elements of the present invention achieved high efficiency and long lifetime, compared with comparative examples.

Example 3

<<Preparation of Full Color Display Device>>
(Preparation of Blue Light Emitting Element)

Organic EL element 1-9 of Example 1 was employed as a blue light emitting element.

(Preparation of Green Light Emitting Element)

Organic EL element 2-4 of Example 2 was employed as a green light emitting element.

(Preparation of Red Light Emitting Element)

A red light emitting element was prepared in the same manner as Organic EL Element 1-1 in Example 1, except that the host compound was replaced with CBP, and the dopant was replaced with Ir-14. The resulting element was employed as a red light emitting element.

Figure 2:
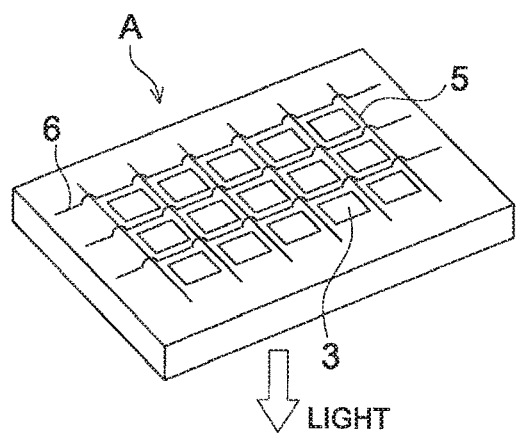
FIG. 2 is a schematic drawing of display section.

The red, green, and blue light emitting organic EL elements, prepared as above, were arranged parallel on one substrate, and an active matrix system full-color display device which had the configuration, shown in FIG. 1, was prepared. In FIG. 2, shown is a schematic view of display section A of the above prepared display device.

Namely, on one substrate, arranged is a wiring section incorporating a plurality of scanning lines 5 and data lines 6, and a plurality of parallel pixels 3 (pixels in the red light emitting region, pixels in the green light emitting region, and pixels in the blue light emitting region), and each of scanning lines 5 and a plurality of data lines 6 of the wiring section is composed of electrically conductive materials. Scanning lines 5 and data lines 6 are orthogonalized in a reticular pattern and connect to pixels 3 in each of the orthogonalized positions (not shown in detail).

The aforesaid plurality of pixels 3 is driven via an active matrix system provided with an organic EL element corresponding to each of the emitted light colors and each of the switching transistors and the drive transistors. When scanning signals are transmitted from scanning lines 5, image data signals are received from data lines 6, and light emission occurs depending on the received image data.

By appropriately arranging parallel red, green, and blue pixels, a full-color display device was prepared.

By driving the above full-color device, it was noted that sharp full-color images with high luminance and high durability were prepared.

Example 4

<<Preparation of White Light Emitting Element and White Light Illuminating Device>>

The electrode of the transparent electrode substrate underwent patterning in an area of 20 mm×20 mm, and, a 40 nm thick α-NPD film was formed thereon as a positive hole injection/transport layer in the same manner as Example 1. Further, eclectic current was independently applied to each of the aforesaid heating boat in which Exemplified Compound 1 was placed, the boat in which Exemplified Compound 1-75 was placed, and the boat in which Ir-4 was placed, and vapor deposition was carried out to result in a film thickness of 30 nm, while regulating the vapor deposition rate to 100:5:0.6, respectively, whereby a light emitting layer was arranged.

Subsequently, a 10 nm BCP film was formed, whereby a positive hole inhibition layer was arranged. Further, a 40 nm Alq$_3$-film was formed, whereby an electron transport layer was arranged.

Subsequently, in the same manner as Example 1, square shaped perforated stainless steel mask having the almost same shape as the transparent electrode was arranged on the electron transport layer, and a 0.5 nm lithium fluoride film as a cathode buffer layer and a 150 nm aluminum film as a cathode were formed via vapor deposition.

By employing the resulting element, a flat lamp having a sealed structure similar to that in Example 1 was prepared in the same manner as Example 1. When electric current was applied to the resulting flat lamp, it emitted nearly white light, whereby it was noted that it was usable as an illuminating device.

The invention claimed is:

1. An organic electroluminescent element comprising a substrate having thereon at least an anode and a cathode, and a light emitting layer between the aforesaid anode and the aforesaid cathode, wherein at least one light emitting layer incorporates a compound represented by Formula (A):

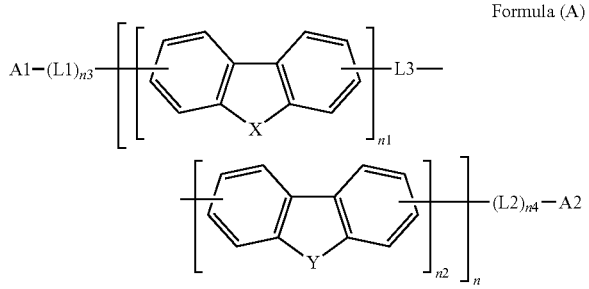

Formula (A)

wherein A1 and A2 each represent a hydrogen atom or a nitrogen-atom containing substituent, provided that at least one of A1 and A2 represents one selected from the group consisting of a carbazolyl group, a carbolinyl group; represented by Formula (a), and a diarylamino group; X and Y each represents O; L1 and L2 each represent a divalent linking group; and L3 represents a divalent linking group selected from the group consisting of carboline ring, a diazacarbazole ring, a triazole ring, a pyrrole ring, a pyridine ring, a pyrazine ring, a quinoxaline ring, a triophene ring, an oxadiazole ring, and an indole ring; n represents an integer of 1 or 2; n1 and n2 each represent an integer of 1 or 2; and n3 and n4 each represent 0 or 1;

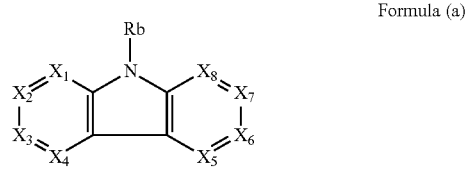

Formula (a)

Wherein $X_1$-$X_8$ each represent a nitrogen atom or —C(Ra)═; at least one of the aforesaid $X_1$-$X_8$ represents —C(Ra)═, wherein Ra is a hydrogen atom; and Ra and Rb each represent a hydrogen atom or a substituent.

2. The organic electroluminescent element of claim 1, wherein the at least one of A1 and A2 represents a carbazolyl group or a diarylamino group.

3. The organic electroluminescent element of claim 1, wherein L3 represents a divalent linking group selected from the group consisting of a pyridine ring and an oxadiazole ring.

4. The organic electroluminescent element of claim 1, wherein L3 represents a divalent linking group derived from a pyridine ring.

5. The organic electroluminescent element of any claim 1, wherein the aforesaid light emitting layer incorporates a phosphorescence emitting metal complex.

6. The organic electroluminescent element of claim 4, wherein the aforesaid phosphorescence emitting metal complex is an Ir complex.

7. The organic electroluminescent element of claim 4, wherein the aforesaid phosphorescence emitting metal complex is represented by Formula (B):

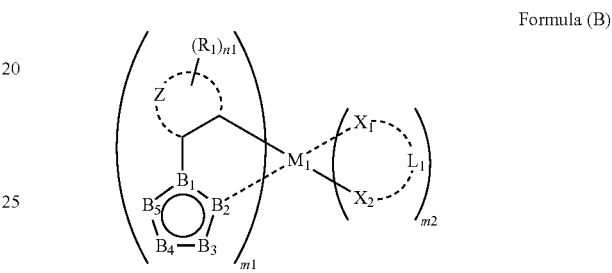

Formula (B)

wherein $R_1$ represents a substituent; Z represents a group of non-metal atoms necessary for forming a 5-7 numbered ring; $n_1$ represents an integer of 0 -5; $B_1$- $B_5$ each represents a carbon atom, a nitrogen atom, an oxygen atom, or a sulfur atom and at least one represents a nitrogen atom; $M_1$ represents a metal of Groups 8 -10 in the element periodic table; $X_1$ and $X_2$ each represents a carbon atom, a nitrogen atom, or an oxygen atom; $L_1$ represents a group of atoms which form a bidentate ligand with $X_1$ and $X_2$; m1 represents 1, 2, or 3; and m2 represents 0, 1, or 2, provided that a sum of m1 and m2 is 2 or 3.

8. The organic electroluminescent element of claim 6, wherein m2 of the phosphorescence emitting metal complex represented by the aforesaid Formula (B) is 0.

9. The organic electroluminescent element of claim 7, wherein a nitrogen-containing heterocyclic ring formed by phosphorescence emitting metal complexes $B_1$-$B_5$ in the aforesaid Formula (B) is an imidazole ring.

10. The organic electroluminescent element of claim 1, emitting white light.

11. A display device provided with the organic electroluminescent element of claim 1.

12. An illuminating device provided with the organic electroluminescent element of claim 1.

* * * * *